(12) United States Patent
Takakura et al.

(10) Patent No.: US 6,462,185 B1
(45) Date of Patent: Oct. 8, 2002

(54) FLORAL ORGAN-SPECIFIC GENE AND ITS PROMOTER SEQUENCE

(75) Inventors: Yoshimitsu Takakura; Tsuyoshi Inoue; Hideaki Saito; Toru Ito, all of Shizuoka-ken (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/125,891

(22) PCT Filed: Dec. 26, 1997

(86) PCT No.: PCT/JP97/04892

§ 371 (c)(1),
(2), (4) Date: Aug. 27, 1998

(87) PCT Pub. No.: WO98/29542

PCT Pub. Date: Jul. 9, 1998

(30) Foreign Application Priority Data

Dec. 27, 1996 (JP) ................................................ 8-349505

(51) Int. Cl.[7] ........................ C07H 21/02; C07H 21/04; C12P 21/06; C12N 9/24; C12N 9/42
(52) U.S. Cl. ..................... 536/23.1; 536/23.2; 435/69.1; 435/200; 435/209; 435/252.3; 435/320.1; 530/350
(58) Field of Search ................................ 435/69.1, 200, 435/209, 252.3, 320.1; 536/23.1, 23.2; 530/350

(56) References Cited

FOREIGN PATENT DOCUMENTS

| JP | 6 510662 | 12/1994 |
|----|----------|---------|
| WO | 9 213956 | 8/1992 |
| WO | 9 502319 | 1/1995 |

OTHER PUBLICATIONS

Gunther Busam et al., *Plant Physiol.*, (1977) 115: 1029–1038.
Qun Qhu et al., *Bio/Technology*, vol. 12, pp. 807–812, Aug. 1994.
Beatrice Iseli et al., *Plant Physiol.*, (1993) 103: 221–226.
*Breed Sci.*, vol. 48 (Suppl. 1), pp. 281 (1998).
H. Harikrishna et al., *Plant. Molecular Biology*, 30: 899–911 (1996).
Thomas Wemmer et al., *Planta*, (1994) 194: 264–273.
Alan D. Neale et al., *The Plant Cell*, vol. 2, pp. 673–684 (Jul. 1990).
Ivan Mikaelian et al., *Nucleic Acids Research*, vol. 20, No. 2, p. 376 (1992).
Yuhong Zhou et al., *Nucleic Acids Research*, vol. 19, No. 21, p. 6052 (1991).
Mark J. Zoller et al., *Nucleic Acids Research*, vol. 10, No. 20, pp. 6487–6500 (1982).
Tohru Tsuchiya et al., *Plant Molecular Biology*, 26: 1737–1746 (1994).
Royce Mohan et al., *Plant Molecular Biology*, 22: 475–490 (1993).
Valdis A. Dzelzkalns et al., *The Plant Cell*, vol. 5, pp. 855–863 (Aug. 1993).
Fumio Takaiwa et al., *Plant Molecular Biology*, 16: 49–58 (1991).
John G. Verburg et al., *The Journal of Biological Chemistry*, vol. 267, No. 6, pp. 3886–3893 (Feb. 25, 1992).
Nishizawa, Y., et al., "Sequence variation differential expression and clomosomal location of rice chitinase genes", Mol.Gen.Genet. (1993) vol. 241, Nos.1, 2, pp.1–10.
Zhu, Q., et al., "Isolation and characterization of a rice gene encoding a basic chitinase" Mol.Gen.Genet. (1991) vol. 226, No. 1, 2, pp.289–296.
Xu, Y., et al., "Regulation, expression and function of a new basic chitinase gene in rice (*Oryza sativa* L.)", Plant Molecular Biology (Feb., 1996) vol. 30, No. 3, pp.387–401.
Kim, Y.K., et al., "Isolation and characterization of cDNA clones encoding class I chitinase in suspension cultures of rice cells", Biosci. Biotech. Biochem. (1994) vol. 58, No. 6 pp. 1164–1166.
Anuratha, C. S., et al. "Induction of chitinases . . . in *Rhizoctonia solani*–infected rice plants:isolation of an infection–related chitinase cDNA clone" Physiologa Plantarum (May, 1996) vol. 97, No. No. 1, pp.39–46.

*Primary Examiner*—Tekchand Saidha
(74) *Attorney, Agent, or Firm*—Birch, Stewart, Kolasch & Birch, LLP

(57) ABSTRACT

The flower organ-specific promoter is contained in the sequence consisting of nucleotides of positions from 1 to 1234 in the nucleotide sequence represented by SEQ ID NO:3. The promoter includes sequences derived from the above sequence by deletion, substitution, insertion or addition of one or more nucleotides and having a flower organ-specific promoter activity and also those obtainable by using the nucleotide sequence represented by SEQ ID NO:1 as a probe and having a flower organ-specific promoter activity.

11 Claims, 13 Drawing Sheets

A

B

Structure of promoter region of RPC175 gene
The number above each base indicates the relative location taking the location of the most upstream transcription initiation point as +1.

Alignment of the restriction enzyme maps of RPG102 and RPC175
Thick lines indicate the nucleotide sequences of the clones while thin lines indicate the nucleotide sequences of the vectors. Shaded parts indicate the nucleotide sequences of introns.
Ec refers to EcoRI, P refers to PstI, pBS refers to pBluescript and AAAA .... refers to polyA.

Analysis on organ-specificity of GUS expression in transformants having construct for analyzing promoter expression.

The abscissa refers to the organ tested while the ordinate refers to the number of transformants showing GUS expression. Dotted parts indicate the number of individuals showing spotty GUS expression.

A

B

← 175 protein

| incubation temperature | 15 | 25 | 37 | (°C) |
|---|---|---|---|---|
| IPTG Concentration | 0.1 | 0.5 | 2 | (mM) |

| amount of 175 protein (A) | 97.6 | 12.4 | 2.1 | (ng) |
|---|---|---|---|---|
| total amount of eluted proteins (B) | 38 | 24 | 34 | (μg) |
| A/B | 2.57 | 0.52 | 0.06 | (%) |

US 6,462,185 B1

FLORAL ORGAN-SPECIFIC GENE AND ITS PROMOTER SEQUENCE

This application is the national phase under 35 U.S.C. §371 of prior PCT International Application No. PCT/JP97/04892 which has an International filing date of Dec. 26, 1997 which designated the United States of America, the entire contents of which are hereby incorporated by reference.

TECHNICAL FIELD TO WHICH THE INVENTION BELONGS

This invention relates to a gene showing specific expression in monocotyledon flower organs and its promoter sequence. This invention further relates to a chitinase acting as a defensive mechanism against pathogenic bacteria and a chitinase gene.

PRIOR ART

There have been reported some cases of the isolation of genes which are expressed specifically in flower organ, for example, anther-specific genes and pistil-specific ones. However, only a few genes specific to another have been reported as genes which are isolated from monocotyledons and for which the promoter sequences have been clarified. These reports are exemplified by JP (Kohyo) HEI 6-504910, Tsuchiya et al. Plant Mol. Biol. 26, 1737–1746, 1994, etc. in which the nucleotide sequences of rice anther-specific genes, their expression profiles, etc. are indicated.

Promoters exhibiting expression specifically in flower organ are required in order to artificially improve the morphology of plant flower organs, in particular germ organs, or physiological phenomena or to analyze functions of various genes in flower organs. In monocotyledons which represent major cereals, however, few genes expressed exclusively in flower organs have been isolated hitherto. In particular, there has been reported no promoter sequence showing predominant expression in pistil which is the female germ organ or lodicule which regulates flowering.

Although chitinase (EC 3.2.1.14), which seemingly acts as a defensive mechanism against pathogenic bacteria and fungi, can be cited as an example of genes expressed in flower organ, most of the chitinases of plant origin reported so far are constitutively expressed not only in flower organs but also in roots (see, for example, Neale et al. The Plant Cell, 2, 673–684, 1990). Exceptionally, chitinases such as potato SK2 (Wemmer et al. Planta 194, 264–273, 1994) and tomato Chi2;1 (Harikrishna et al. Plant Molecular Biology, 30, 899–911, 1996) show style-specific expression.

On the other hand, there have been isolated some chitinases of monocotyledons. For example, Zhu ant Lamb (Mol. Gen. Genet., 226, 289–2961991) isolated a chitinase called RCH10 from rice and reported that the gene of this enzyme was constitutively expressed in root under aseptic conditions. Further, Zhu et al. (BIO/TECHNOLOGY, 12, 807–812, 1994) constructed tobacco with enhanced tolerance to pathogenic bacteria by using the above-mentioned gene together with an alfalfa glucanase gene.

There has been no report in monocotyledons, however, about a chitinase which is not expressed at a detectable level in root, being expressed exclusively in flower organs.

SUMMARY OF THE INVENTION

An object of the present invention is to provide a novel flower organ-specific promoter sequence enabling genetic manipulations of pistil or lodicule which were impossible in the prior art particularly in monocotyledons.

Another object of the present invention is to provide a novel chitinase which makes it possible to impart to plants a general resistance against pathogenic bacteria and fungi containing chitin.

DETAILED DESCRIPTION OF THE INVENTION

Figure 1:
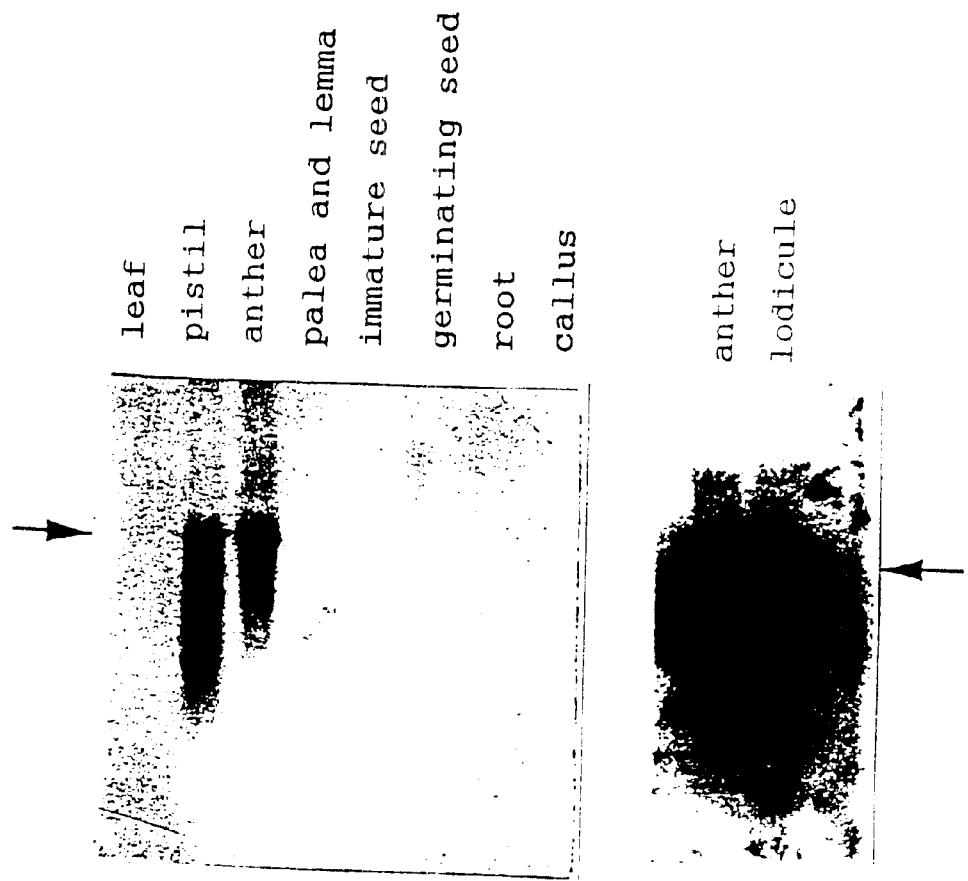
FIG. 1 consists of photographs showing the results of Northern analysis on RPC175 gene.

The present inventors have conducted an extensive search and, as a result, discovered the DNA fragment comprising the sequence having the nucleotides of positions 1–1234 in the nucleotide sequence represented by SEQ ID NO:3, a part of this sequence or a sequence derived from these sequences by deletion, substitution, insertion or addition of one or more nucleotides and having a promoter activity, thus solving the above-mention problem.

Thus, in accordance with the present invention, the above mentioned problem can be solved also by identifying a monocotyledon flower organ-specific promoter sequence in a rice genome library with the use of the nucleotide sequence represented by SEQ ID NO:1 as a probe.

Furthermore, the present inventors have solved the above-mentioned problem by the DNA sequence encoding a chitinase comprising the nucleotides of positions 114–1097 in the nucleotide sequence represented by SEQ ID No:1, a part of said sequence, or a DNA sequence having a sequence derived from these nucleotide sequences by deletion, substitution, insertion or addition of one or more nucleotides and encoding a protein having biological activity equivalent to that of the protein encoded by a DNA consisting of the above-mentioned nucleotide sequence, or a sequence of chitinase consisting of the amino acid sequence represented by SEQ ID NO:2, a part of this sequence or an amino acid sequence of chitinase having a sequence derived from these amino acid sequences by deletion, substitution, insertion or addition of one or more amino acids.

Now, the present invention will be described in greater detail.

As described above, the first invention found by the present inventor relates to a DNA comprising the sequence having the nucleotides of position 1–1234 in the nucleotide sequence represented by SEQ ID NO:3, a part of said sequence or a sequence derived from these sequences by deletion, substitution, insertion or addition of one or more nucleotides and having a promoter activity.

The promoter sequence of the present invention, namely, the sequence comprising the nucleotides of positions 1–1234 in the nucleotide sequence represented by SEQ ID NO:3 has no substantial homology to any known promoter sequence. Thus, this sequence is considered to be novel. This sequence can be isolated from a natural monocotyledonous plant in accordance with the method described in, for example, Example 2 as will be given hereinafter.

The DNA fragment of the present invention has a promoter activity specific to flower organs. The term "flower organ-specific promoter activity" as used herein means that the expression of the promoter activity the DNA fragment of the present invention in flower organs (anther, filament, pistil and lodicule), in particular in flowering period, is more prominent than in other organs (at least leaf, root, callus, germinating seed, immature seed and palea and lemma). It has been confirmed that the DNA fragment of the present invention is flower organ-specific in monocotyledons and there is a possibility that it may be flower organ-specific in other plants too.

The nucleotide sequence represented by SEQ ID NO:3 has the following characteristics among others.
1. It has 3 transcription initiation points at intervals of several nucleotides and these points are all A (adenine) following TC. Specifically, the transcription initiation points are the adenines (A) at positions 1122, 1125 and 1129.
2. There is a TATA box-like sequence (5'-TATATAA-3') (Corden et al. Science 209, 1406–1414, 1980) 30 bp upstream of the most upstream transcription initiation point.
3. There are 2 ATG sequences in the same reading frame, each being located 77 bp and 113 bp downstream of the most upstream transcription initiation point.
4. A termination codon (TGA) is located 21 bp upstream of the most upstream ATG (the first ATG). Moreover, there are two poly A signal-like sequences(5'-AATAAA-3') (Heidecker and Messing, Annu. Rev. Plant Physiol. 37, 439–466, 1986) in the terminator region. The term "terminator region" herein referrs to the region which is downstream of the termination codon.

A SnaBI cleavage site is found between positions 1135 and 1140 while a PstI cleavage site exists between positions 1223 and 1228. The region following position 1235 is the structural gene region.

It has been found in accordance with the present invention that the promoter is located in the region upstream of the structural gene, i.e., in the region comprising the nucleotides of positions 1–1234 in the nucleotide sequence represented by SEQ ID NO:3. However, sequences comprising a part of this region are also included in the present invention, so long as they have a similar promoter activity.

For example, the regions of positions 1–1228 and 1–1140 have the flower organ-specific promoter activity, as will be described in the examples given hereinafter. Thus, these sequences are included in the present invention. Also, it is expected that the region of positions 1–1121 has a similar promoter activity, since a transcription initiation point is located at position 1122 as described above.

Further, it should be noted that the promoter sequence contains an EcoRI site at nucleotide positions 1–6 by chance, which enabled us to determine the promoter sequence starting from this site. Therefore, it is well anticipated that a sequence starting from a nucleotide some what downstream will have the promoter activity. This is so because a number of reports indicate that the tissue- or time-specificity or inducibility of most plant promoters is substantially contained in the region of 0.3 to 0.4 kb which precedes the transcription initiation point. In the promoter of type II glutelin gene of rice, for example, the tissue- and time-specific expression is fully achieved exclusively by the 441 bp fragment before the transcription initiation point (Takaiwa et al. Plant Mol. Biol. 16:49–58, 1991). In the promoter of self-incompatibility-related gene SLG13 of Brassia oleracea, the 411 bp region before the transcription initiation point directs the expression in pistil and pollen (Dzelzkalns et al. The Plant Cell 5:855–863, 1993). In the promoter of anionic peroxidase gene of tomato, the organ-specificity as well as the pathogen and wound-inducibility are determined by the 358 bp region upstream of the transcription initiation point (Mohan et al. Plant Mol. Biol. 22:475–490, 1993). Thus, it is observed for a number of promoters that a part of the reported sequence maintains the full function if only said part is the region comprising nucleotides of several hundred bp preceding the transcription initiation point.

Accordingly, any DNA sequence obtained from the region within several hundred bp, preferably about 500 bp upstream of the transcription initiation point and having the flower organ-specificity characterized in the present invention is included in the present invention. For example, if a region within several hundred bp upstream of the transcription initiation point is easily isolated from rice genome by PCR with the use of primers designed based on the nucleotide sequence of the present invention and the region exhibits the flower organ-specificity inherent to the promoter of the present invention, then the shorter promoter sequence is included in the present invention.

The present invention further includes in the scope thereof DNA fragments having a sequence derived from these sequences by deletion, substitution, insertion or addition of one or more nucleotides and showing the promoter activity.

It is well known that when a nucleotide sequence of a DNA having a physiological activity is slightly modified by deletion, substitution, insertion or addition of one or more nucleotides, the physiological activity of the DNA will be maintained in general. Therefore, the present invention includes within the scope thereof DNA sequences derived from the above mentioned promoter sequence by such slight modification and having the promoter activity. That is to say, the sequence consisting of the nucleotides of positions 1–1234 in the nucleotide sequence represented by SEQ ID NO:3 parts of this sequence having the promoter activity (for example, those consisting of several hundred bp upstream of the transcription initiation point), and DNA sequences derived therefrom by deletion, substitution, insertion or addition of a small number of nucleotides and having the promoter activity are all intended to be included in the scope of the present invention.

Similarly, the sequence consisting of the nucleotides of positions 1–1140 in the nucleotide sequence represented by SEQ ID NO:3, the sequence consisting of the nucleotide sequence of positions 1- to 1121 thereof, and DNA sequences derived therefrom by deletion, substitution, insertion or addition of a small number of nucleotides and having the promoter activity are all included in the scope of the present invention.

The addition, insertion, deletion or substitution of nucleotides can be carried out by, for example, site-directed mutagenesis (see, for example, Nucl. Acids Res. 10:6487–6500, 1982) which is a well-known technique. The expression "one or more nucleotides" as used herein means nucleotides in such a number as to allow addition, insertion, deletion or substitution by the site-directed mutagenesis method.

Site-directed mutagenesis can be performed in the following manner with the use of, for example, a synthetic oligonucleotide primer which is complementary to the single-stranded phage DNA to be mutated except a specific discordance, i.e., the desired mutation. Namely, a complementary strand is synthesized by a phage with the use of the above-mentioned oligonucleotide as a primer. Next, a host bacterium carrying the phage is transformed by the double-stranded DNA thus obtained. The culture of the transformed bacterium is then plated onto agar and plaques containing the phage from a single cell are formed. Thus theoretically 50% of the newly formed colonies will contain the phage carrying the mutation in the single strand while the remaining 50% of the colonies have the original sequence. The plaques thus obtained are hybridized with a synthetic probe having been treated with kinase at such a temperature as to allow the hybridization of the plaques coinciding with the DNA having the desired mutation as described above but not with those having the original strands. Then the plaques hybridized with the probe are picked up and cultured to subsequently recover the DNA.

In addition to the above site-directed mutagenesis method, nucleotide(s) can be substituted, deleted, added or inserted into the promoter sequence while maintaining its activity by treating the gene with a mutagen or by selectively cleaving the gene and then deleting, adding or substituting the desired nucleotide(s) followed by ligation.

Also, the substitution, deletion, addition or insertion of specific nucleotide(s) may be conducted by the site-directed mutagenesis with the use of the PCR method (Mikaelian et al. Nucl. Acids Res. 20:376, 1992) or the random nucleotide substitution technique (Zhou et al. Nucl. Acids Res. 19:6052, 1991) by taking advantage of the low fidelity of Taq DNA polymerase.

Now, the second invention found by the present inventors will be illustrated.

The second invention of the present invention relates to a monocotyledon flower organ-specific promoter sequence which is contained in a sequence identified from a rice genome library with the use of the nucleotide sequence represented by SEQ ID NO:1 as a probe.

This nucleotide sequence represented by SEQ ID NO:1 can be obtained by constructing a cDNA library from rice (Oryza sativa) palea and lemma or pistil, isolating a cDNA which is expressed specifically in pistil, anther and lodicule by differential screening and determining the whole nucleotide sequence thereof. The nucleotide sequence thus determined may be used as a probe as a whole. Alternatively, use may be made of a part thereof as a probe. In this case, any hybridization and washing conditions are employable so long as they enable the formation of a molecular hybrid if the nucleotide sequence of the DNA to be identified has a homology of 80% or more to the nucleotide sequence represented by SEQ ID NO:1.

The genome library of rice is constructed by using rice (Oryzae sativat) green leaf, though the present invention is not limited thereto. The promoter sequence is identified from the library thus obtained by using the above-mentioned probe. In order to determine that the promoter is specific to flower organs, a chimera gene is constructed by ligating β-glucuronidase (GUS) gene to the promoter sequence. The resultant chimera gene is introduced into rice plant and then the expression sites are confirmed.

The determination of the above-mentioned nucleotide sequence represented by SEQ ID NO:1, the construction of the rice genomic library and the assessment of the specific promoter activity are described in detail in Examples as will be given hereinafter, though the present invention is not limited thereto.

As described above, the nucleotide sequence represented by SEQ ID NO:3, in particular, the sequence comprising the nucleotides of positions 1–1234 is a novel DNA fragment isolated by the present inventors. Based on the disclosure of the present invention, those skilled in the art can easily isolate DNA fragments having a flower organ-specificity similar to the one of the present invention from various monocotyledon genome libraries with the use of at least a part of the nucleotide sequence comprising the nucleotides at positions 1–1234 of the nucleotide sequence represented by SEQ ID NO:3. The conditions for hybridization with the probe can be appropriately determined too. Therefore, the present invention includes within the scope thereof DNA fragments which are hybridizable with at least a part of the nucleotide sequence consisting of the nucleotides of positions 1–1234 of SEQ ID NO:3 and have a flower organ-specific promoter activity similar to that of the present invention.

The promoter of the present invention is a novel flower organ-specific promoter which makes it possible to genetically manipulate and improve not only anther but also pistil and lodicule which was previously impossible particularly in monocotyledons. Thus the promoter is useful for, e.g., the following purposes.

(1) Creation of female sterile plants by use of a structural gene capable of inducing sterility wherein said gene is ligated to the promoter sequence of the present invention or a part thereof.

(2) Flower organ-specific enlargement or elongation by use of a structural gene capable of promoting the elongation or division of plant cells wherein said gene is ligated to the promoter sequence of the present invention or a part thereof.

(3) Genetic regulation of flowering by means of the expression of the promoter of the present invention in lodicule.

(4) Providing the whole flower organs or a part thereof with an improved tolerance to herbicides or diseases by use of a gene imparting tolerance to herbicides or resistance to diseases wherein said gene is ligated to the promoter.

The promoter of the present invention is expressed in the stigma, style, anther wall, filament and lodicule of rice in the flowering period. When this promoter is used, for example, in the improvement of male sterile rice, its expression in anther wall and filament can be ignored. Further, it is sometimes expected that the sensitivity to a gene product varies from organ to organ. In such a case, the promoter of the present invention will be useful, for example, to specifically improve stigma and style or lodicule.

Finally, the third invention established by the present inventors will be illustrated.

The third invention relates to a DNA sequence which comprises the nucleotides of positions 114–1097 in the nucleotide sequence represented by SEQ ID NO:1 or a part of said sequence, or a DNA sequence derived therefrom by deletion, substitution, insertion or addition of one or more nucleotides and encoding a protein having a biological activity equivalent to that of the protein encoded by the DNA consisting of the above-mentioned nucleotide sequence. The third invention further relates to a sequence consisting of the amino acid sequence represented by SEQ ID NO:2, a part of this sequence or an amino acid sequence derived from these amino acid sequences by deletion, substitution, insertion or addition of one or more amino acids and having a biological activity equivalent to that of the protein consisting of the above-mentioned amino acid sequence.

The DNA sequence of the present invention, i.e., the sequence consisting of the nucleotides of positions 114–1097, and the amino acid sequence represent a novel chitinase having homologies of 67 to 69% and 54 to 61%, respectively to the known rice class I chitinase.

The amino acid sequence represented by SEQ ID NO:2 has the following characteristics.

By analogy based on the probable homologies to various class I chitinases, its structure is supposed to have the following elements from the N-terminal side thereof: a leader sequence having consecutive hydrophobic amino acid residues (amino acids of positions 1–20 in SEQ ID NO:2) at the N-terminus; a chitin-binding region rich in cysteine residues (amino acids of positions 21–61 in SEQ ID NO:2) in the N-terminus region of the mature protein; and a spacer region (amino acids of positions 62–83 in SEQ ID NO:2) followed by the catalytic region (amino acids of positi84–328 in SEQ ID NO:2). In this catalytic region, the first tyrosine residue (Verburg et al. J. Biol. Chem., 267, 3886–3893, 1992; Y at position 199 in SEQ ID NO:2) in NYNYG (amino acids at positions 198–202 in SEQ ID NO:2), which is considered as the active site of chitinase, is conserved. At the C-terminus, characteristic consecutive amino acid residues (at positions 318–328 in SEQ ID NO:2) showing no homology to other rice chitinases are observed. The molecular weight and isoelectric point of the mature protein region (from positions 21 to 328 in SEQ ID NO:2) are calculated respectively as about 32 kD and 7.24.

When mature protein region (amino acids of positions 21–328 in SEQ ID NO:2) is expressed in $E.\ coli$ and the chitinase activity is measured as one of the biological activities thereof, the chitinase activity can be detected in practice.

As discussed above, a plant class I chitinase has a cysteine-rich chitin-binding region which is followed by a spacer region at the N-terminus of the mature protein. However, Iseli et al. (Plant Physiol. 10221–226, 1993) reported that the chitinase and antimicrobial activities are maintained in the absence of these regions. Accordingly, it is highly probable that the chitinase of the present invention also has chitinase activity exclusively in the catalytic region, namely, without the chitin-binding and the spacer regions. Therefore, it is expected that the catalytic region consisting of the amino acids of positions 84–328 in SEQ ID NO:3 should have a biological activity equivalent to those of the entire 175 protein (amino acids of positions 1–328 in SEQ ID NO:2) or the mature protein (amino acids of positions 21–328 in SEQ ID NO:2). Thus, this region is also included in the present invention.

As described above, the novel chitinase of the present invention has chitinase activity and thus is useful for the following purposes:

(1) Production of disease or insect damage-resistant plants by way of the transformation of plant cells by the DNA sequence comprising the nucleotides of positions 114–1097 in the DNA sequence represented by SEQ ID NO:1 of the present invention or a part thereof, wherein said DNA sequence or a part thereof has been ligated to a constitutive, tissue-specific, time-specific or inducible promoter.

(2) Application of chitooligosaccharides produced by the chitinase as materials for manufacturing foods, cosmetics and drugs.

EXAMPLES

Example 1

Isolation of Flower Organ-specific cDNA

Paddy rice varieties "Akihikari", "Tsukinohikari" and "IR24" were grown in a greenhouse and subjected to the following experiments.

(1) Extraction of RNA

The leaf, pistil, anther, lodicule, palea and lemma, immature seed, germinating seed, root and callus of "IR24" and palea and lemma (4.5 to 6.0 mm in length) of "Akihikari" were collected, immediately frozen in liquid nitrogen and then stored at −80° C. A portion of the pistil was divided into the stigma and ovary tissues.

Figure 2:
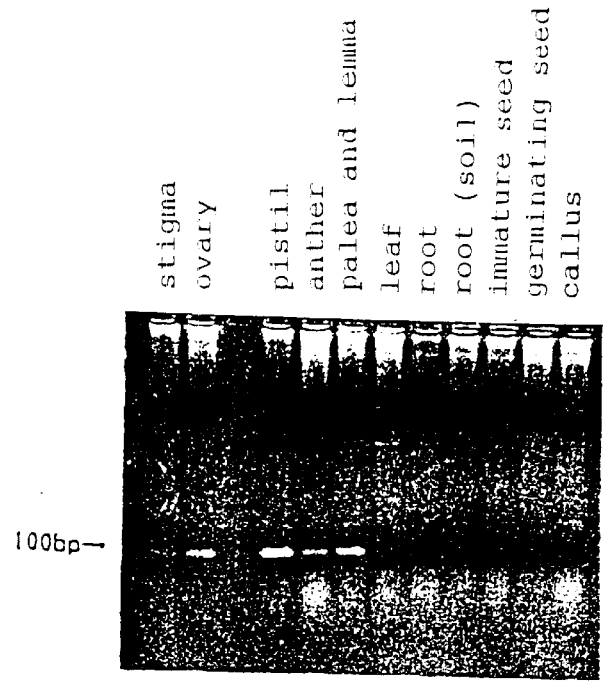
FIG. 2 consists of photographs showing the results of RT-PCR analysis on RPC175 gene.
Figure 2:
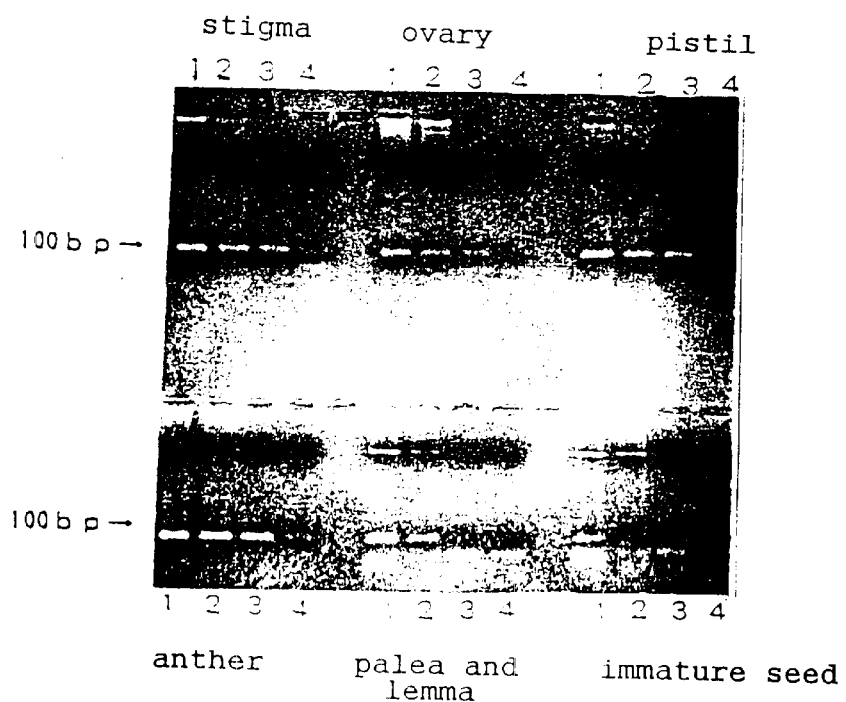

The total RNA was extracted from these tissues by the SDS-phenol method of Watanabe and Price (Proc. Natl. Acad. Sci. USA, 79, 6304–6308, 1982) except that β-mercaptoethanol was added as an antioxidant to the extraction buffer to give a final concentration of 10% (V/V). The tissues to be used in the reverse transcription PCR experiment were treated with DNase I (FPLC pure, manufactured by Pharmacia) in the presence of RNase inhibitor (RNAguard, manufactured by Pharmacia), rather than being subject to lithium chloride precipitation, so as to minimize the contamination with any trace amount of DNA. The leaf and root [expressed in "root (soil)" in FIG. 2 and Table 1 as will be given hereinafter] were collected from a plant grown for 1 month in the greenhouse after sowing. The pistil, anther, lodicule and palea and lemma were collected from a plant immediately to several days before flowering. The immature seed was collected from a plant 1 to 2 weeks after flowering. The germinating seed and root were obtained from a plant aseptically grown on an N6 medium (Chu et al. Scientia Sinica, 18, 659–668, 1975) respectively for 1 and 3 weeks after sowing.

The callus was induced from a seed in an N6 solid medium containing 2 mg/l of 2,4-D and then cultured before use in a liquid medium of the same composition under shaking for 1 week. The total RNA of the pistil and leaf was purified to provide polyA+RNA by using Oligotex-dT30 super (manufactured by Takara Shuzo Co., Ltd.) in accordance with the manufacturer's instructions (2) Construction of Palea and Lemma and Pistil cDNA Libraries About 2.2 μg and 1 μg of respective polyA+RNA isolated and purified from palea and lemma and pistil was employed as a template to synthesize the cDNA by using ZAP-cDNA Synthesis Kit (manufactured by STRATAGENE). The determination of RI uptake ratio indicated that about 462 ng and about 55 ng of the first strand cDNA of the palea and lemma and pistil were reversely transcribed by the oligo-dT priming, and about 1,022 ng and about 72 ng of the second strand cDNA were synthesized directly from the first strands. In accordance with the manufacturer's instructions, the cDNA was connected to an EcoRI adaptor and digested with XhoI, to be ligated into vector Uni-ZAPXR. Next, the phage DNA was packaged into phage particles by using Giga-pack Gold packaging extract (manufactured by STRATAGENE). The phage was transfected into *E. coli* PLK-F' host cells, which were then inoculated on a plate and each library size was examined. As a result, the palea and lemma CDNA library size was calculated as 1×106 pfu (plaque forming unit) while that of the pist cDNA library was calculated as $3 \times 10^6$ pfu.

(3) Differential Screening

Differential screening was carried out basically in accordance with the method of Gasser et al. (The Plant Cell 1, 15–24, 1989). About 2,000 pfu of the phage from the palea and lemma cDNA library was infected into *E. coli* PLK-F' cells and the cells were plated on square petri dishes (14×10 cm). For each plate, a replica filter was prepared with the use of a nylon membrane filter Hybond-N+(manufactured by Amersham) and the filter was treated in accordance with the manufacturer's instructions.

As the probes for hybridization, use was made of single-stranded cDNA synthesized from about 100 ng of the polyA+RNA (or about 2 µg of the total RNA) of pistil and leaf. To 2 µl of an RNA solution, 0.5 mM of d(ATG)TP, 10 mM of DTT and 133 M-MuLV buffer (manufactured by BRL) were added. Next 30 ng/µl of Random DNA Hexamer (manufactured by Pharmacia) [or 80 ng/µl of Oligo dT Primer (manufactured by Amersham)] was added thereto (the concentration indicates the final concentration in each case). After dissociating the secondary structure of the RNA by heating at 65° C. for 5 minutes, the primer was annealed at room temperature. After further adding 1.5 unit/µl of RNase inhibitor (RNAguard, manufactured by Pharmacia), 10 unit/µl of reverse transcriptase M-MuLV (manufactured by BRL) and 4 µCi/µl of [α-$^{32}$P]dCTP (each expressed in the final concentration), the liquid reaction mixture of 20 µl in total was maintained at 37° C. for one hour. Subsequently, RI-unlabeled dCTP was further added to give a final concentration of 0.5 mM and the reaction was continued for 30 minutes.

The labeled DNA probes were purified by using Quick Spin Column G-50 Sephadex (manufactured by BOEHRINGER MANNHEIM). The probes were denatured by adding an equivalent amount of 2 N NaOH (final concentration: 1 N). The filter was first treated in a hybridization buffer (0.25 M $Na_2HPO_4$ pH 7.2, 7% SDS, 1 mM EDTA, 133 Denhardt's solution) at 68° C. for 10 minutes. Then the single-stranded probes (final concentration: 0.2–0.3×10$^7$ cpm/ml) and carrier.DNAs (0.1 mg/ml, salmon sperm DNA, 0.1 µg/ml λDNA, 0.1 µg/ml rice DNA) were added thereto and hybridization was performed at 68° C. overnight (16 to 24 hours).

The filter was washed in the buffer (20 mM $Na_2HPO_4$ pH 7.2, 1% SDS, 1 mM EDTA) at room temperature twice and at 68° C. twice each for 15 minute. Next, this filter was exposed to Kodak X-Omat Film at –70° C. for 4 to 5 days. When about 20,000 plaques were examined, 114 plaques showing intense hybridization signals with the pistil probe but only weak or background signals with the leaf probe were selected by the primary screening. Subsequently, these plaques were further purified and 41 plaques were selected in the tertiary screening stage.

Among these plaques, one showing a particularly weak signal with the leaf probe (indistinguishable from the background) was stored in 200 µl of SM buffer (0.1 M NaCl, 7 mM $MgSO_4$, 50 mM Tris-CL, pH 7.5, 0.01% gelatin) containing one drop of chloroform at 4° C. Then the thus stored liquid was diluted and the phage was plated so as to give a considerably low plaque density (10 to 100 pfu/plate). A plaque separated from others was isolated and stored in the same buffer. From this liquid, a lysate (plating lysate) containing the phage at a high concentration was prepared and in vivo excision was performed in accordance with the instructions attached to ZAPcDNA Synthesis Kit. Thus a plasmid [pBluescriptSK(-)] was cut from the phage genome. Then it was digested with restriction enzymes EcoRI and XhoI (manufactured by Takara Shuzo Co., Ltd.) and thus a cDNA insert (about 0.8 kb) was isolated and purified.

(4) Analysis on Organ-specific Expression of cDNA Clones i) Northern Hybridization Analysis The cDNA clone selected in the above (3) was subjected to Northern hybridization to examine the expression patterns and expression levels in various organs. Filters were prepared in the following manner. First, the secondary structure of the total RNA (20 µg) from each of the organs described in the above (1) was dissociated in accordance with the method of Sambrook et al. (Molecular Cloning, 1982) with the use of deionized Glyoxal and DMSO and then fractionated in a 1% agarose gel. Next, the RNA was blotted onto a nylon membrane Gene Screen Plus (DU PONT) by the convention capillary transfer method. After drying in a vacuum oven at 80° C. for 1 hour, the filter was boiled in 20 mM Tris-Cl (pH 8.0) for 5 minutes to thereby remove Glyoxal therefrom. As a probe, the 0.8 kb EcoRI fragment of the above-mentioned cDNA was RI-labeled by using Multiprime Labeling System (manufactured by Amersham).

Pre-hybridization and hybridization were carried out in accordance with the manufacturer's instructions attached to the filter. The filters were washed with 2×SSC, 1% SDS and 0.2×SSC, 1% SDS at room temperature each for 5 minutes, then with 0.16×SSC, 1% SDS at 65° C. for 15 minutes twice and then with 2×SSC at room temperature for 1 minute. Subsequently the filters were exposed to Kodak X-Omat Film at –70° C. overnight. As a result, signals were observed exclusively in the lanes of pistil, anther and lodicule while the other lanes showed no signal, as shown in FIG. 1. Thus, it was clarified that the differential clone isolated above was expressed strongly in pistil, anther and lodicule but in very or extremely low level in other organs. The size of the transcripts was estimated to be 1.5 kb.

Then the expression doses were determined by measuring the signal densities with a densitometer. As a result, the relative expression levels in anther and lodicule were respectively about 2 and about 4, taking that in pistil as 1.

ii) Reverse Transcription PCR Analysis

To analyze the organ-specific expression of the cDNA clone at a higher precision, reverse transcription PCR was carried out by using RNA of various rice organs as templates. First, the partial nucleotide sequence of the cDNA was determined. By using GENESIS 2000 Fluorescence Sequencer (manufactured by Du Pont), the nucleotide sequence of the cDNA inserted into the plasmid pBluescript SK(-) was determined. In accordance with the manufacturer's instructions attached to the Sequencer, T7 DNA polymerase reaction was performed by using RV and M4 primers (manufactured by Takara Shuzo Co., Ltd.) of M13 followed by electrophoresis on 6% acrylamdie gel. Then, the nucleotide sequence was determined from both the 5'- (EcoRI) an3'-(XhoI) sides.

On the basis of about 300 nucleotides in the 5'-side of this DNA, appropriate primers:

5'-GACACCCGCAAGCGTGA-3' (75RV1 (SEQ ID NO:10): 17-mer) and

5'-CCCTTCACCTCCTTGTA-3' (75FW1 (SEQ ID NO:11); 17-mer);

were synthesized with DNA Synthesizer (manufactured by ABI) and purified by OPC Cartridge (manufactured by ABI) for the reverse transcription PCR experiment. With these primers, a product of 101 bp was amplified.

Further, the following primers synthesized based on the sequence of rice actin 1 gene (Racl, McElroy et al. Plant Mol. Biol. 14, 163–171, 1990

5'-GTATCCATGAGACTACATACAACT-3' (24-mer) (SEQ ID NO:12) and

5'-TACTCAGCCTTGGCAATCCACA-3' (22-mer) (SEQ ID NO:13);

were used as controls. These primers were selected so that an intron would be included therebetween. Therefore, it was intended that if the template DNA was contaminated with genomic DNA, a product (350 bp) of the genomic DNA would be amplified along with the product (267 bp) of the cDNA The total RNA of each of the above-mentioned organ was serially diluted (1 μg, 30 ng, 1 ng, 30 pg) and treated at 65° C. for 5 minutes to thereby dissociate the secondary structure. After quenching on ice, it was incubated in a reaction mixture comprising 1×Perkin Elmer Gene Amp-buffer 1 mM dNTPmix, 5 ng/μl oligo dT15 primer (manufactured by Amersham), 2.5 mMgCl$_2$, 3 U/μl RNase inhibitor (RNAguard, manufactured by Pharmacia) and 1 U/μl reverse transcriptase M-MuLV (manufactured by BRL) (each concentration referrs to the final concentration) at 37° C. for 30 minutes. Next, it was treated at 95° C. for 5 minutes to dissociate the RNA-CDNA hybrid and then cooled on ice. Then a pair of primers (10–20 pmoles), 10×buffer and 1 unit of AmpliTaq Polymerase (manufactured by Perkin Elmer) were added and the reaction mixture of 50 μl in total volume was subjected to PCR for 40 cycles with each cycle consisting of 1 minute at 94° C., 1 minute at 60° C. and 2.5 minutes at 72° C.

As a control experiment, the reverse transcription product (i.e., total RNA) prepared from each organ was subjected to PCR with the use of primers for Racl gene, which is considered to be constitutively expressed in all organs in rice. As a result, the anticipated PCR product (267 bp) was detected from all of the organs examined. This indicated that no template cDNA preparations employed were contaminated with substantial amount of genomic DNA. The detection limits (amount of template RNA) in germinating seed and root were 0.5 μg and 1 ng respectively, while the limits in other organs were 30 ng. Supposing that Rac1 gene was expressed in all of the organs tested herein at the same level, it was estimated that the reverse transcription PCR efficiencies in germinating seed and root were respectively about 1/17 and about 30, taking that in pistil as 1, while those in other organs were almost the same as that in pistil.

Subsequently, a reverse transcription PCR experiment was carried out by using clone-specific primers which had been preliminarily proved to amplify the product of expected molecular weight by using plasmid clones. When the cDNA reversely transcribed from 1 μg of RNA was used as a template in PCR, the expected product (101 bp) was detected from pistil, anther, immature seed and palea and lemma, as shown in FIG. 2A. Namely, no PCR product was amplified from cDNA of other organs. In the case of pistil, the expression was observed both in stigma and ovary. In each organ from which the PCR product was detected, the template RNA was diluted and the expression level was estimated. As a result, in pistil (stigma and ovary) and anther, the PCR product was amplified from the most minimum quantity of the template (30 pg). In contrast, the PCR product was amplified from 30 ng or above, and 1 μg of the template in palea and lemma, and immature seed, respectively (FIG. 2B).

When the expression level in pistil (stigma and ovary) was taken as 1, therefore, the level in anther was estimated as about 1 while those in palea and lemma and immature seed were calculated respectively as $10^{-3}$ and $3 \times 10^{-5}$. That is to say, this gene was expressed only at an extremely low level in organs other than flower organs. Table 1 summarizes the results of the reverse transcription PCR and the Northern analysis.

TABLE 1

Relative expression dose of RPC175 in various organs estimated from Northern analysis and reverse transcription PCR (referring the dose in stigma or pistil as to 1)

| Organ | pistil | (stigma | ovary) | anther | lodicule | leaf |
|---|---|---|---|---|---|---|
| Northern analysis | 1 | (NT | NT) | 2 | 4 | 0 |
| RT-PCR | 1 | (1 | ≦1) | 1 | NT | 0 |

| Organ | root | root (soil) | germinating seed | callus |
|---|---|---|---|---|
| Northern analysis | 0 | NT | 0 | 0 |
| RT-PCR | 0 | 0 | 0 | 0 |

| Organ | palea and lemma | immature seed |
|---|---|---|
| Northern analysis | 0 | 0 |
| RT-PCR | $10^{-3}$ | $3 \times 10^{-5}$ |

NT: not analyzed.

(5) Genomic Southern Hybridization Analysis

One month after sawing, genomic DNA was isolated and purified by the phenol SDS method (Komari et al. Theor. Appl. Genet. 77, 547–552, 1989) from paddy rice plants of the varieties of "Tsukinohikari" and "IR24". About 5 μg of DNA was digested with restriction enzymes BamHI, EcoRI, HindIII, PstI, SalI and XhoI (manufactured by Takara Shuzo Co., Ltd.) and the DNA fragments were fractionated in a 0.8% agarose gel. After blotting the DNA onto a nylon membrane filter HybondN+ (Amersham), genomic Southern hybridization was carried out with the use of the above-mentioned cDNA fragment of 0.8 kb which had been RI-labeled similar to the above (4)i).

The hybridization and the subsequent washing were effected according to the manufacturer's instructions attached to the filter. As a result, several faint bands were observed in addition to one or two intense bands (FIG. 3), though the hybridization was effected under conditions that would not allow any hybridization to take place unless the genomic DNA had a high homology to the probe. That is to say, when digested with EcoRI, for example, a strong signal (2.6 kb) and three weak signals of 1.6 kb were detected. It was considered that such a faint band might have a somewhat short homologous region to the probe or might not have high homology to the probe. These results indicate that the cloned gene may have a few related sequences in rice genome.

(6) Isolation of Full-length cDNA

The pistil cDNA library [Example 1 (2)] was screened with the use of the cDNA clone of 0.8 kb as a probe. About 1.6×10⁵ pfu of the phage containing the pistil cDNA was plated on 8 square petri dishes in the same manner as that of Example 1 (3) and replica filters were prepared. These filters were subjected to hybridization with the above CDNA (0.8 kb) which had been RI-labeled with the use of Multiprime Labeling System (manufactured by Amersham). As a result, 40 positive plaques were obtained by the primary screening. Among these plaques, 20 were subjected to in vivo excision and plasmids containing the cloned cDNA were cut out from phage DNA.

Subsequently, these plasmids were digested with EcoRI and the cDNA clones were excised. When these clones were compared with each other, the longest ones (3 clones) were about 1.25 kb in size. One typical clone was selected therefrom and the nucleotide sequence of about 300 bp at the 3'-side was determined. When compared with the corresponding region of the clone of 0.8 kb from "Akihikari" employed as a probe, the nucleotide sequences of these clones almost completely coincided with each other including the 3'-untranslated region.

To examine in detail whether or not the obtained clone (1.25 kb) and the clone (0.8 kb) originated from the same gene, a pair of primers as follows were synthesized based on the nucleotide sequence determined above:

5'-GACATCATGTCGGCGTCTGCG-3' (175RV1 (SEQ ID NO:14); 21-mer) and

5'-GCCATGACCATGCATACATATGG-3' (175FW1 (SEQ ID NO:15); 23-mer).

Then reverse transcription PCR was effected for all of the rice organs in the same manner as the one employed in Example 1 (4) ii) but for 30 cycles. The results thus obtained were the same as those obtained in the case of the clone of 0.8 kb.

Accordingly, it was clarified that the gene of the present invention was expressed almost exclusively in pistil, anther and lodicule. The expression level thereof in palea and lemma and immature seed were about 1/1,000 times as much as the expression level in pistil, anther and lodicule, while no detectable level of expression was observed in other organs. These facts clarified that the selected cDNA clone of 1.25 kb had the same origin as that of the cDNA of 0.8 kb isolated by the differential screening. Thus, this cDNA clone was employed as the probe in the subsequent isolation of genomic clones. This cDNA clone of 1.25 kb was named "RPC175".

(7) Determination of the Nucleotide Sequence of RPC175

The entire nucleotide sequence of the cDNA clone RPC175 (about 1.25 kb), which is expressed specifically in flower organs, was determined in the following manner with the use of Fluorescence Sequencer (Model 373A, manufactured by Applied Biosystems). By using the M13 primers RV (5'-side of the cDNA, decoding the sense strand) and M4 (3'-side of the cDNA, decoding the antisense strand) on the plasmid vector pBluescript SK(-) carrying RPC175 integrated thereinto, the nucleotide sequences of about 250 to 300 bp in the 5'- and 3'-sides were first determined.

Based on the nucleotide sequence information thus obtained, internal primers were constructed and the nucleotide sequences of the sense strand and antisense strand were decoded from both sides. Next, further primers were synthesized based on the partial nucleotide sequences thus decoded and the nucleotide sequences of the sense strand and antisense strand were consecutively decoded. Thus, 9 internal primers (4 for the sense strand and 5 for the antisense strand) were used in total including the primers used in the reverse transcription PCR. On the other hand, it was known by restriction analysis that RPC175 had two ApaI sites. Thus, RPC175 was split into 3 fragments at these sites and subcloned into the same site of the plasmid vector pBluescript SK(-). Then the nucleotide sequence was determined by the M13 primers.

Thus the entire nucleotide sequence of RPC175 was determined by using the internal primers and the subcloning. Next, the nucleotide sequence thus determined was analyzed by using GENETYX-MAC8.0, a software for analyzing nucleotide sequence/amino acid sequence. As a result, it was found that the complete nucleotide sequence of RPC175 consisted of 1,258 bp and had 2 initiation codons (ATG), separated by a sequence of 36 bp, in the same reading frame in the 5'-side and the upstream ATG was located immediately after a sequence capable of forming a stem loop.

The reading frame as determined by the ORF analysis enabled estimation of amino acids. Thus, it was determined that 340 amino acids were encoded when the translation was initiated from the upstream ATG, while 328 amino acids were encoded when the translation was initiated from the downstream ATG. Two polyA signals (5'-AATAAA-3') were located downstream of the termination codon. The entire nucleotide sequence of RPC175 is represented by SEQ ID NO:1. It is to be understood that the first 60 bp region originate in the genome clone as will be described hereinafter and that SEQ ID NO:1 includes all the nucleotides from the transcription initiation point to polyA.

The amino acid sequence encoded by RPC175 is represented by SEQ ID NO:2. As will be described hereinafter, it was highly probable that of the two ATGs the downstream ATG was the transcription initiation point. Thus, the amino acid sequence consisting of 328 amino acids in total from the downstream ATG to the termination codon is shown in SEQ ID NO: 2. In the amino acid sequence represented by SEQ ID NO:2, the sequence consisting of the amino acids of positions 1–20 is estimated to be the leader sequence while the sequence after the leader is the amino acid sequence of the mature protein, as will be illustrated hereinafter.

A homology analysis was conducted by the software GENETYX-MAC/CD 32 and BLAST, an internet program for nucleotide sequence detection. As a result, RPC175 was homologous to class I chitinases of rice, wheat, barley, corn, potato and tomato. That is, it showed homology over the entire regions, excepting for the variable region (amino acids of positions 62–83 in SEQ ID NO:2), including the leader sequence with consecutive hydrophobic amino acids (positions 1–20), the chitin-binding region rich in cysteine (positions 21–61) and the catalytic region (positions 84–328). The catalytic region contained the first tyrosine residue in NYNYG (Y at position 199 in the amino acid positions 198–202 positions in SEQ ID NO:2) which is conserved in a number of basic chitinases and considered as the active site. At the C-terminus, characteristic consecutive amino acids (amino acids positions 318–328 in SEQ ID NO:2) were observed unlike other rice chitinases. RPC175 showed homologies to various rice class I chitinases of about 67 to 69% based on the nucleic acids and about 54 to 61% based on the amino acids.

The molecular weight and isoelectric point of the mature protein (amino acids of positions 21–328 in SEQ ID NO:3) were calculated respectively to be about 32 kD and 7.24.

Example 2

Isolation of Promoter (1) Construction of Genomic Library

Genomic DNA was isolated by the SDS-phenol method, and purified by the lithium chloride precipitation method for elimination of RNA from rice leaves about 2 months after sowing. As a preliminary test, the DNA was first partly digested with a restriction enzyme MboI (manufactured by Takara Shuzo Co., Ltd.) to determine the digestion conditions which would allow the formation of fragments of 16 to 23 kb in apparent size. Next, the genomic DNA was digested under the so determined reaction conditions and subjected to sucrose density gradient centrifugation. Sucrose was dissolved in a buffer (20 mM Tris-HCl pH 8.0, 1 mM EDTA, 200 mM NaCl) to give a gradient of 5 concentrations (10, 17.5, 25, 32.5 and 40%). These sucrose solutions were layered in this order in a centrifugation tube (40PA, manufactured by Hitachi) and finally the partly digested DNA solution was layered on top of the gradient. After centrifuging at 20,000 rpm for 17 hours at 20° C. by using a rotor SRP28 SA (manufactured by Hitachi), the mixture was divided into 80 portions (0.5 ml each) with a peristaltic pump (AC-2110, manufactured by Atto) to provide a fraction containing DNA fragments of 16 to 23 kb in the largest amount.

This DNA fraction was then ligated with a vector LAMBDA DASH II/BamH(manufactured by STRATAGENE) by the action of T4 DNA ligase (manufactured by BOEHRINGER MENNHEIM) and then packaged into phage particles by using Gigapack II Gold packaging extract (manufactured by STRATAGENE). Thus, a rice genomic library was constructed, the size of which was calculated as about $5 \times 10^6$ pfu.

(2) Screening of Clones

About 10,000 pfu of the phage was mixed with *E. coli* SRBP2 for infection and inoculated into a square petri dish (14×10 cm). After an incubation at 39° C. overnight, a nylon membrane filter Hybond N+ (manufactured by Amersham) was brought into contact with the plaque surface and then processed in accordance with the manufacturer's instructions attached to the filter. The probe was a 1.2 kb EcoRI fragment of the rice flower organ-specific cDNA (RPC175) which was used after being RI-labeled with the use of Multiprime Labeling System (manufactured by Amersham). Thus, plaque hybridization was carried out. The hybridization and washing were effected under the same conditions as those specified in the above Example 1 (3) provided that 1×Denhardt's solution and carrier DNAs were not employed. From about 160,000 plaques, 35 positive clones were selected in the primary screening. Subsequently, the secondary screening was performed to give 12 positive clones.

Next, phage DNAs were prepared from these plaques. They served as templates, in the PCR which was performed with the use of the RPC175-specific primers 175FW1 and 175RV1 as in the foregoing reverse transcription PCR. From the PCR experiment using gene-specific primers, the target clones were screened. As a result, the expected product of about 200 bp was found to have been amplified in 8 clones out of 12. Five clones among them were further subjected to PCR by using another set of primers (75FW1 and 75RV1). As a result, a product longer by about 90 bp than the one amplified by using cDNA as a template was amplified in every case.

Subsequently, the nucleotide sequence was determined for the PCR products of these 5 clones at 2 sites (about 400 bp in total). When compared with the nucleotide sequence of the control cDNA, these 5 genomic clones all showed a homology of 99% or above except the intron sequence. Based on these facts, it was concluded that these clones most probably represented the genomic clone which was the target of this screening.

The product obtained by using 75FW1 and 175RV1 had an intron of 85 bp having a 5'-GT-AG-3' sequence in the both ends thereof. Therefore, when the DNA of the genomic clone was employed as a template, a PCR product longer than that amplified by using cDNA as a template was amplified. This intron had a PstI site at the 3'-terminus.

(3) Subcloning of Gene Region

Figure 3:
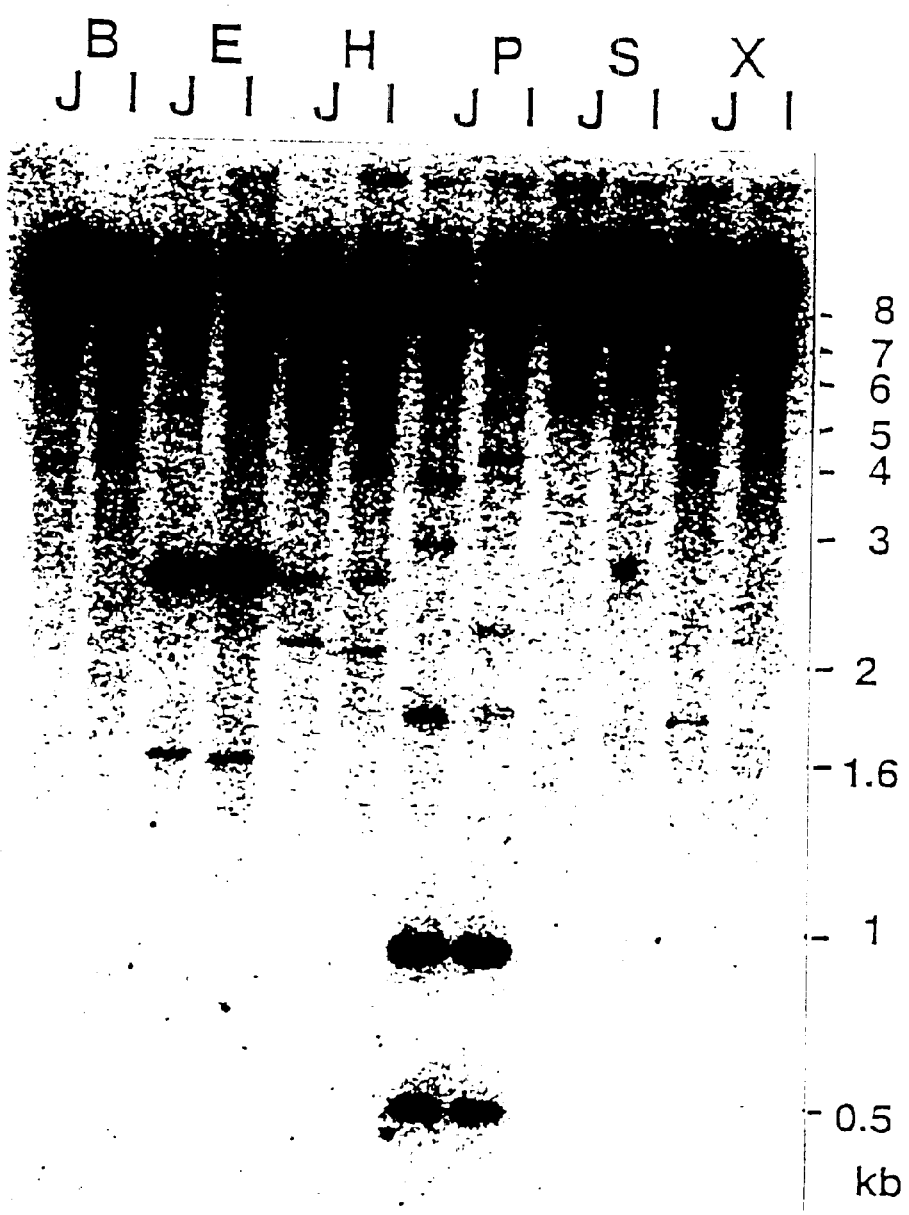
FIG. 3 consists of a photograph showing the results of genomic Southern analysis on RPC175 gene.

The total genomic DNA of rice was digested with a restriction enzyme EcoRI and genomic Southern analysis was carried out by using the RPC175 gene as a probe. Thus a band with a weak signal appeared at about 1.6 kb in addition to the one with a strong signal at about 2.6 kb (FIG. 3). On the other hand, phage DNA was extracted from the above-mentioned 5 clones and digested with EcoRI followed by Southern hybridization with the use of RPC175 as a probe. As a result, it was found that the DNA fragments which formed hybridization with RPC175 were limited to those of 2.6 kb and 1.6 kb, which agreed with the results of the Southern analysis on the genomic DNA. It was known from the nucleotide sequence data, that RPC175 had the unique EcoRI site about 70 bp upstream of the 3'-terminus. Therefore, the 1.6 kb fragment with a weak signal was considered to have been detected due to the homology between the short region (about 70 bp) from the EcoRI to the poly A sites in the 3'-region of RPC175 cDNA employed as a probe and the genomic DNA fragment.

From the signal intensity in the genomic Southern analysis, it was anticipated that the 2.6 kb EcoRI fragment would include the complete structural gene region and at least about 1 kb upstream thereof, unless it contained a large intron. Thus, this fragment was subcloned into the plasmid vector Bluescript SK(–) and named "RPG102". For further analysis, RPG102 was digested with a restriction enzyme PstI and electrophoresed on an agarose gel, whereby, RPC102 was divided into 4 fragments of about 1.2, 0.8, 0.4 and 0.2 kb.

Next, these DNA fragments were transferred onto a filter and subjected to Southern analysis with the use of RPC175 as a probe. As a result, signals were detected in 3 (about 0.8, 0.45 and 0.1 kb) out of the 4 fragments. It was known from the nucleotide sequence data that RPC175 had a PstI site about 45 bp downstream of the 5'-terminus and another PstI site about 120 bp downstream thereof. Thus, the band of 0.1 kb in size detected by the Southern analysis was assignable to this region. It was also known that another PstI site was located about 50 bp upstream of the EcoRI site at the 3'-terminus, and in addition, an analysis with the use of restriction enzymes indicated that the distance between the second PstI site in the 5'-side and the PstI site in the 3'-side was about 0.95 kb. Accordingly, it was assumed that RPG102 contained an intron of about 200 bp in addition to the above-mentioned intron of 85 bp, and that the fragment of 1.25 kb was cut into the fragments of 0.8 kb and 0.45 kb at the PstI site in the intron of 85 bp.

Based on these facts, it was considered that the 3 bands detected by the Southern analysis corresponded to the structural gene region and that the promoter region was contained in the PstI fragment of 1.2 kbp which did not form a molecular hybrid with RPC175 cDNA.

(4) Identification of Promoter Region

By analyzing the nucleotide sequence in the 5'-side of RPC175 cDNA, it was clarified that two ATGs were contained in the same reading frame in this region of RPC175.

A primer containing the downstream ATG:

5'-CTTCATGGCCACCTGCAGGTTTGC-3' (C5FW (SEQ ID NO:16); 24-mer) was synthesized and the nucleotide sequence of about 300 bp in the 3'-side of the promoter region of RPG102 was determined.

To ensure the determination of the transcription initiation point by the primer extension method, another primer of about 40 bp upstream of C5F 5'-TGCGATCATGGCAAGATGC-3' (p3FW2 (SEQ ID NO:17); 19-mer) was synthesized.

These primers (10 pmole each) were RI-labeled at the 5'-terminus by phosphorylation with the use of [γ-$^{32}$P]ATP according to the manufacturer's instructions attached to MEGARABEL kit (manufactured by Takara Shuzo Co., Ltd.). 0.1 pmole (0.3×10$^6$ cpm) of these labeled primers and 20 μg of the total RNA of pistil or leaf were annealed in the presence of 3 U/μl of RNase inhibitor (RNAguard, manufactured by Pharmacia) in a buffer (0.25 M KCl, 2 mM Tris-HCl pH 8.0, 0.2 mM EDTA) in a reaction system of 10 μl at 40° C. for 2 hours. After adding 30 μl of another buffer (66 mM Tris-HCl pH 8.3, 6.6 mM MgCl$_2$, 1.3 mM DTT, 0.66 mM dNTP, 130 μg/ml actinomycin D) and 1 μl (200 units) of a reverse transcriptase (M-MuLV, manufactured by BRL), the mixture was incubated at 37° C. for 1 hour. Then ethanol and ammonium acetate were added to allow precipitation to occur. After washing the precipitate with 70% ethanol, the product was air-dried and then dissolved in an electrophoresis buffer which was prepared by mixing the reaction termination solution of T7 Sequencing Kit (manufactured by Pharmacia) with 0.1 M NaOH and 1 mM EDTA (2:1). A ⅓ portion of this solution was heated at 95° C. for 3 minutes and then electrophoresed on a 6% acrylamide gel. By using the same primers, an extension reaction was carried out with T7 Sequencing Kit by using a plasmid containing RPG102 as a template, and the product thus obtained was electrophoresed simulataneously.

Figure 4:
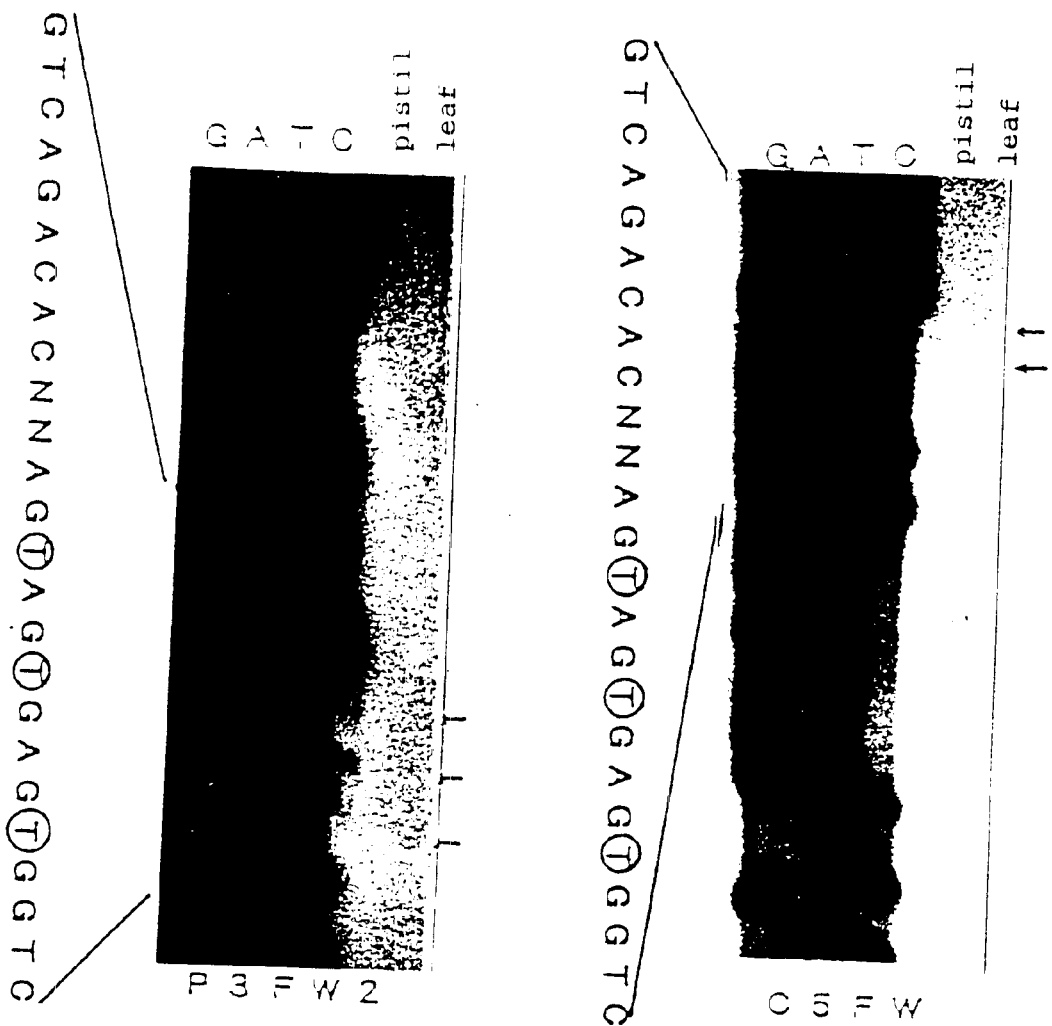
FIG. 4 consists of photographs showing the results of an experiment for determining the transcription initiation point of RPC175 gene by the primer extension method (SEQ ID NO:5).

The results are shown in FIG. 4. No extension product was obtained from leaf RNA in which the gene was not expressed, while 2 bands (in the case of the C5FW primer) and 3 bands (in the case of the P3FW2 primer) of extension products were detected by using the total RNA of pistil as the template. Comparison of the sequence ladders generated side by side indicated that the products by the two primers were detected at the same position in the sequence of RPG 102.

Figure 5:
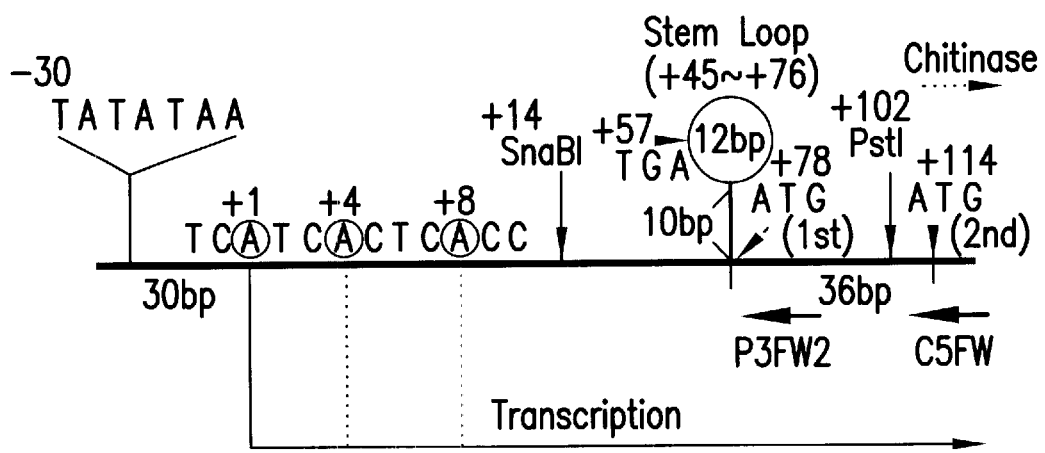
FIG. 5 is a model view showing the structure in the 3' side of the promoter of RPC175 gene (SEQ ID NO:6).

These results indicated that the transcription of RPG102 was initiated from A (adenine) at 3 positions existing at intervals of several bases. A TATA box-like sequence 5'-TATATAA-3' was found 30 bp upstream of the first transcription initiation point (adenine) from the 5'-terminus. The location of the TATA box-like sequence coincided with genes of other plant (Joshi, Nucleic Acids Res., 15, 6643–6653, 1987). Moreover, as described above, the two ATG translation initiation codons 36 bp apart from each other in the same reading frame were located 77 bp and 113 bp downstream of this transcription initiation point (FIG. 5).
(5) Determination of Whole Nucleotide Sequence of RPG102

Among the fragments formed by digesting RPG102 with PstI in Example 2 (3), the fragments of 1.2, 0.8 and 0.45 kb were subcloned into the same sites of pBluescript. From the PstI 1.2 kb fragment containing the promoter sequence, among the above-mentioned fragments, deletion clones with stepwise deletion of 100 to 200 bp were prepared from the both strands (20 clones in total) by using a deletion kit kilo-sequence for (manufactured by Takara Shuzo Co., Ltd.) and the nucleotide sequence was determined with the use of M13 primer (manufactured by Takara Shuzo Co., Ltd.) with Fluorescence Sequencer (Model 373A, manufactured by Applied Biosystems). Regarding the fragments of 0.8 kb and 0.45 kb each containing the structural gene, the nucleotide sequences were determined by using the M13 primer (manufactured by Takara Shuzo Co., Ltd.) and the internal primers described in the above Example 1(7). Furthermore, the nucleotide sequence in the 3' region of RPG102 per se was determined by using the M13 primer and the internal primers. Thus, the entire nucleotide sequence of RPG102 was finally clarified.

As a result, it was found that the whole nucleotide sequence of the RPG102 clone consisted of 2,636 bp and, when compared with the nucleotide sequence of the cDNA clone RPC175, two introns (85 bp and 199 bp) were contained in the region of the structural gene. The nucleotide sequences 5'GT and AG3' at both ends were conserved in both of these introns. The nucleotide sequences in the regions other than these introns of the genomic clone RPG102 coincided completely with the cDNA clone RPC175. A poly A signal-like sequence 5'-AATAAA-3' (Heidecker and Messing, Annu. Rev. PlantPhysiol. 37, 439–466, 1986) was located about 90 bp upstream of the EcoRI site in the 3' side and about 40 bp downstream of the translation termination codon TAG.

Figure 6:
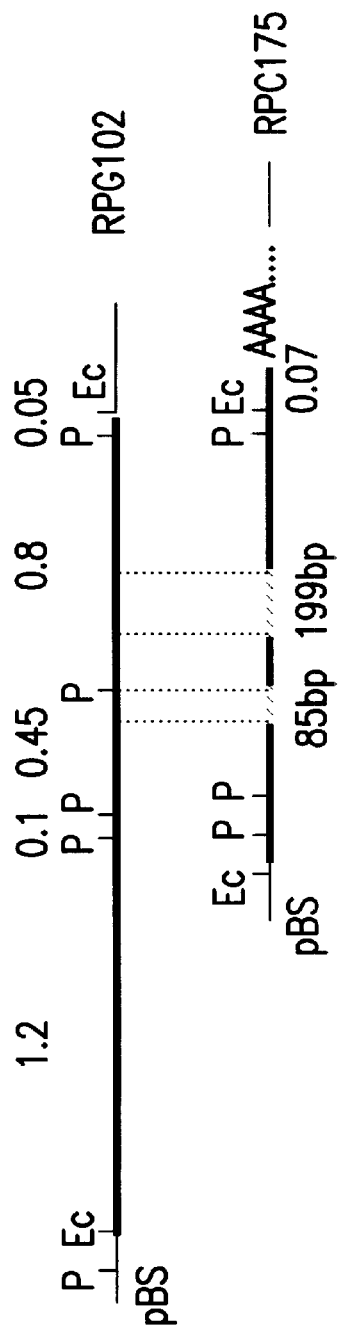
FIG. 6 is a drawing illustrating a comparison of the restriction maps of RPC175 and RPG102.

The entire nucleotide sequence of RPG 102 is represented by SEQ ID NO:3 wherein the sequences in the parentheses are the introns. FIG. 6 shows a comparison of the restriction maps of RPG102 and RPC175.

Example 3

Analysis of Promoter Expression Site
(1) Construction of Vectors for Analyzing Promoter Expression and Transformation of Rice To analyze the expression of the isolated promoter in vivo, vectors having GUS (β-glucuronidase) reporter gene linked thereto were constructed in the following manner. As described above, two ATGs were contained in the same reading frame 77 bp and 113 bp downstream of the most upstream transcription initiation point. Since it was difficult to determine by experiment which of the ATGs was the actual translation initiation point, vectors for analyzing the expression of promoter were constructed for both of these ATGs.

An SnaBI site was located 64 bp upstream of the upstream ATG (the first ATG), i.e., 13 bp downstream of the most upstream transcription initiation point, while a PstI site was located 12 bp upstream of the downstream ATG (the second ATG) (refer to SEQ ID NOS: 1 and 3). These sites, were useful in the construction of the vectors from the plasmid wherein the 1.2 kb PstI fragment containing the promoter region of RPC175 had been integrated into the PstI site of pBluescript as constructed in the step of the nucleotide sequence analysis. In the case of the promoter for analysis of the first ATG, this plasmid was digested with restriction enzymes PstI and SnaBI. Thus a promoter fragment (about 1.1 kb) was cut out therefrom and then the both ends were blunted with DNA Blunting Kit (manufactured by Takara Shuzo Co., Ltd.). In the case of the promoter for the second ATG, the fragment was digested at the restriction sites HindII and XbaI on pBluescript outside the PstI site and thus a promoter fragment (about 1.2 kb) was cut out.

Figure 7:
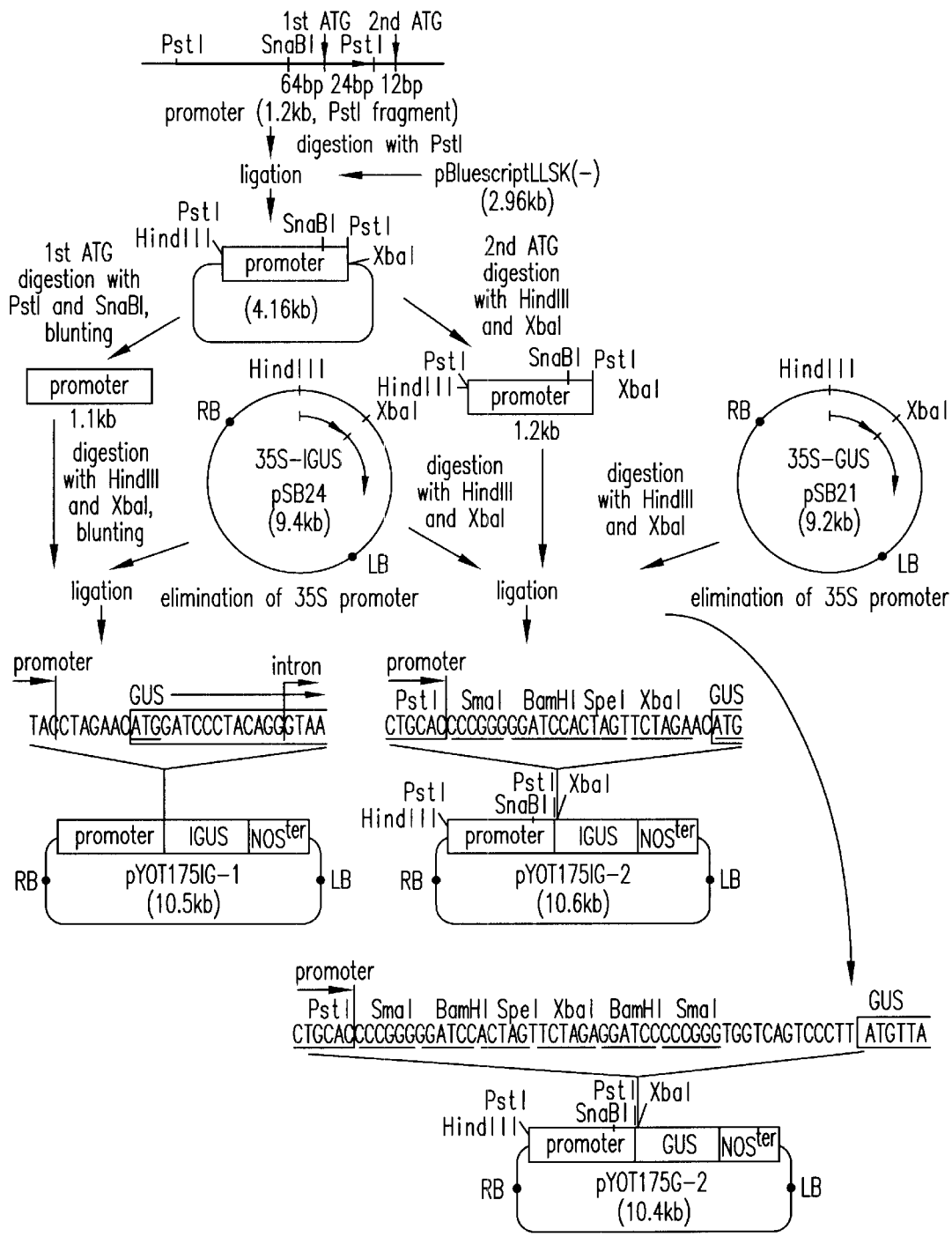
FIG. 7 is a drawing illustrating a procedure for constructing vector for analyzing the promoter expression (SEQ ID NO:7–9).

The vector used in this example was the super binary vector pSB24 (Komari et al. Plant J. 10, 165–174, 1996) for Agrobacterium. This vector contains a GUS structural gene which in turn contains the first intron of castor bean catalase at a downstream of CaMV35S promoter so that the expression level will be increased by the intron. This vector was digested with HindIII and XbaI and the 35S promoter was eliminated therefrom. Then the vector was blunted (for analysis of the first ATG) at its sticky ends or not (for analysis of the second ATG) and ligated respectively with a blunt ended PstI-SnaBI fragment (1.1 kb) or a HindIII-XbaI fragment (1.2 kb) to thereby give vectors pYOT175IG-1 and pYOT175IG-2 each having a structure of RPC175 promoter+IGUS+NOS terminator. In order to check any possibility that the tissue-specificity might be effected by the intron, an additional vector carrying no intron was constructed, particularly in the case of the promoter for the second ATG. To this end, an intron-free super binary vector pSB21 (Komari et al. Plant J. 10, 165–174, 1996) was used. This plasmid was digested with HindIII and XbaI and the 35S promoter was eliminated therefrom. Then it was ligated with the above-mentioned HindIIII-XbaI fragment of about 1.2 kb to thereby give a vector pYOT175G-2 having a structure of RPC175 promoter+GUS+NOS terminator. FIG. 7 illustrates the procedures for constructing these 3 vectors for the expression analysis. With respect to pYOT175IG-2 and pYOT175G-2 among these vectors when the translation of RPC175 was initiated from the upstream ATG in transformed rice cells, frame shifts of −1 type and +1 type occurred respectively, and thus the GUS protein would not be translated.

Each vector thus constructed was transferred from E. coil into Agrobacterium tumefaciens by tri-parental mating. Then these constructs were introduced in parallel into calli developed from immature rice embryo ("Tsukinohikari") together with hygromycin resistance gene by the aid of Agrobacterium in accordance with the method of Hiei et al. (Plant J., 6, 271–282, 1994). The transfer of genes was confirmed by PCR, and the transformants were grown in a greenhouse.

Figure 8:
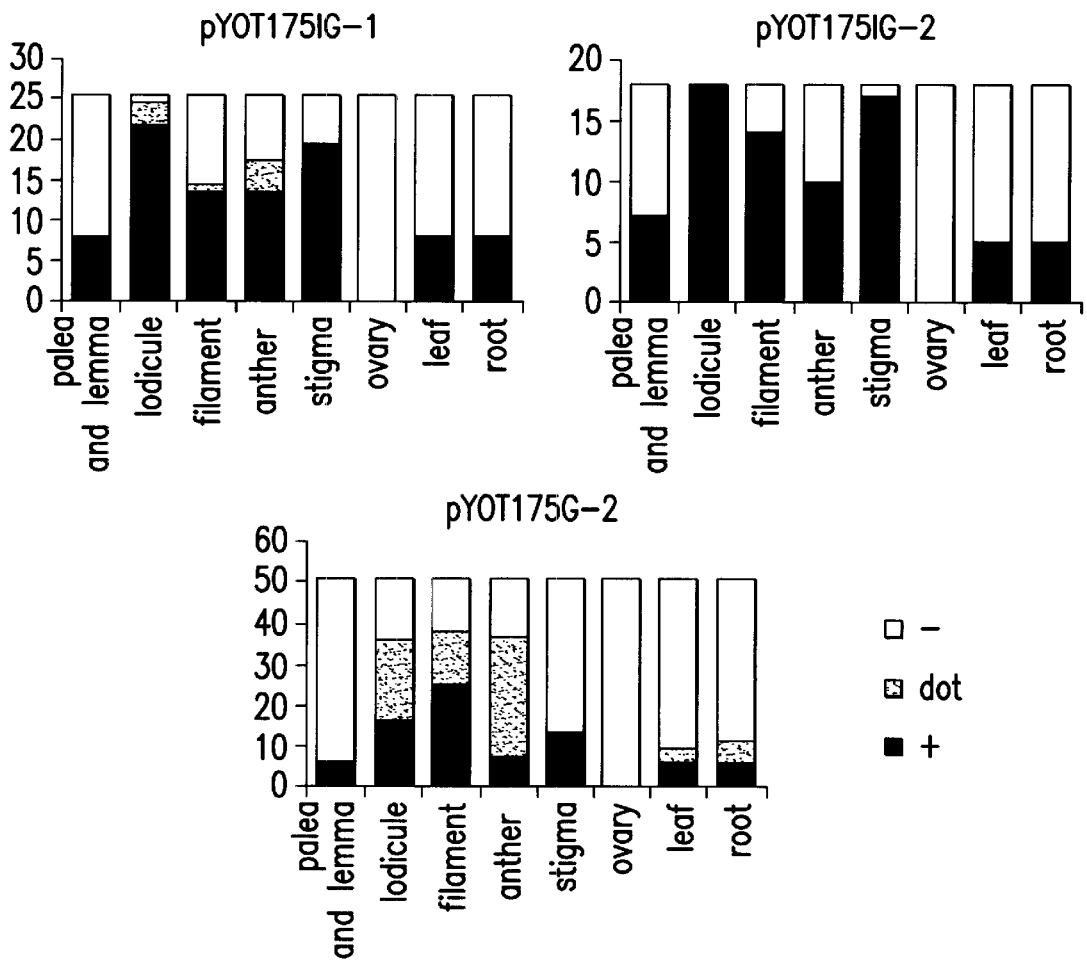
FIG. 8 is a graph showing the results of the analysis on the expression of RPC175 promoter used in combination with GUS.

(2) Analysis of Promoter Expression Site by Way of Histological Observation of GUS According to the method of Jefferson et al. (EMBO J., 6, 3901–3907, 1987), various organs of the rice transformants were stained for GUS with the use of X-gluc. (5-bromo-4-chloro-3-indolyl β-D-glucuronide) as the substrate in order to histologicaly observe the cells under a stereoscopic microscope and an optical microscope. As a result, GUS expression by the RPC175 promoter was observed in pistil stigma, anther, filament and lodicule in most of the transformants in the cases of the intron-inserted constructs (i.e., pYOT175IG-1 and pYOT175IG-2). In some plants, the GUS expression was observed in palea and lemma, leaf or root (FIG. 8).

In the case of the intron-free construct (pYOT175G-2), there were a considerable ratio of individual plants wherein no GUS expression was observed in each organ examined, though the gene transfer was confirmed by PCR and Southern analysis. The expression observed in some individuals was in the form of spot. Moreover, the organ-specificity of expression well coincided with the cases of the intron-inserted constructs (FIG. 8). Thus, it was confirmed that the existence of intron did not substantially change the tissue-specificity.

The fact that GUS expression was observed in pYOT175IG-2 and pYOT175G-2 strongly indicated that the second ATG was the translation initiation point of the RPC175 gene.

Among the transformants showing the GUS expression at least in some of the tissues, the ratios of the transformants showing the GUS expression in all of pistil, anther, filament and lodicule were 81% for pYOT175IG-1, 94% for pYOT175IG-2 and 25% for pYOT175G-2. In the case of each construct, about 50% of these transformants showed no expression in palea and lemma, leaf and root, thus agreeing with the results of Northern analysis and RT-PCR analysis. In FIG. 8, the ordinate refers to the number of transformants showing the expression in the specified organ.

Figure 9:
FIG. 9 consists of photographs showing an example of the results of the analysis on the tissue-specific expression of RPC175 promoter in flower organs.
Figure 9:

In pistil, the GUS expression was observed in stigma axis and branched site. Namely, the GUS gene was not expressed in the cells in the hairy stigma tip (FIG. 9A). On the other hand, no GUS expression was observed in ovary. In stamen, GUS expression was observed at a high frequency in filament, in addition to anther (FIG. 9B). Moreover, GUS was highly expressed in vascular bundle tissues in lodicule and cells therearound (FIG. 9C).

Next, the expression time-specificity at various development stages of flower organs was examined. As a result, the strongest expression was observed in pistil at the heading and flowering time. At the growth stage showing a distance between auricles of the last two leaves of −5 to 5 cm, the pistil of the transformants harboring the construct carrying the inserted intron showed GUS expression. In contrast, the transformants with the intron-free construct showed no GUS expression. These results suggest that the expression of the RPC175 promoter is stronger in the pistil at the flowering time than in the pistil at the time of the differentiation of the hairy tissues in the top of stigma.

Although it remains unknown why the expression was observed in leaf, root or palea and lemma, the position effect of the sites of rice genomes into which T-DNA was integrated or rearrangement of the introduced genes may be accountable for to these results.

(3) Measurement of Promoter Activity by GUS Fluorescent Assay

Figure 10:
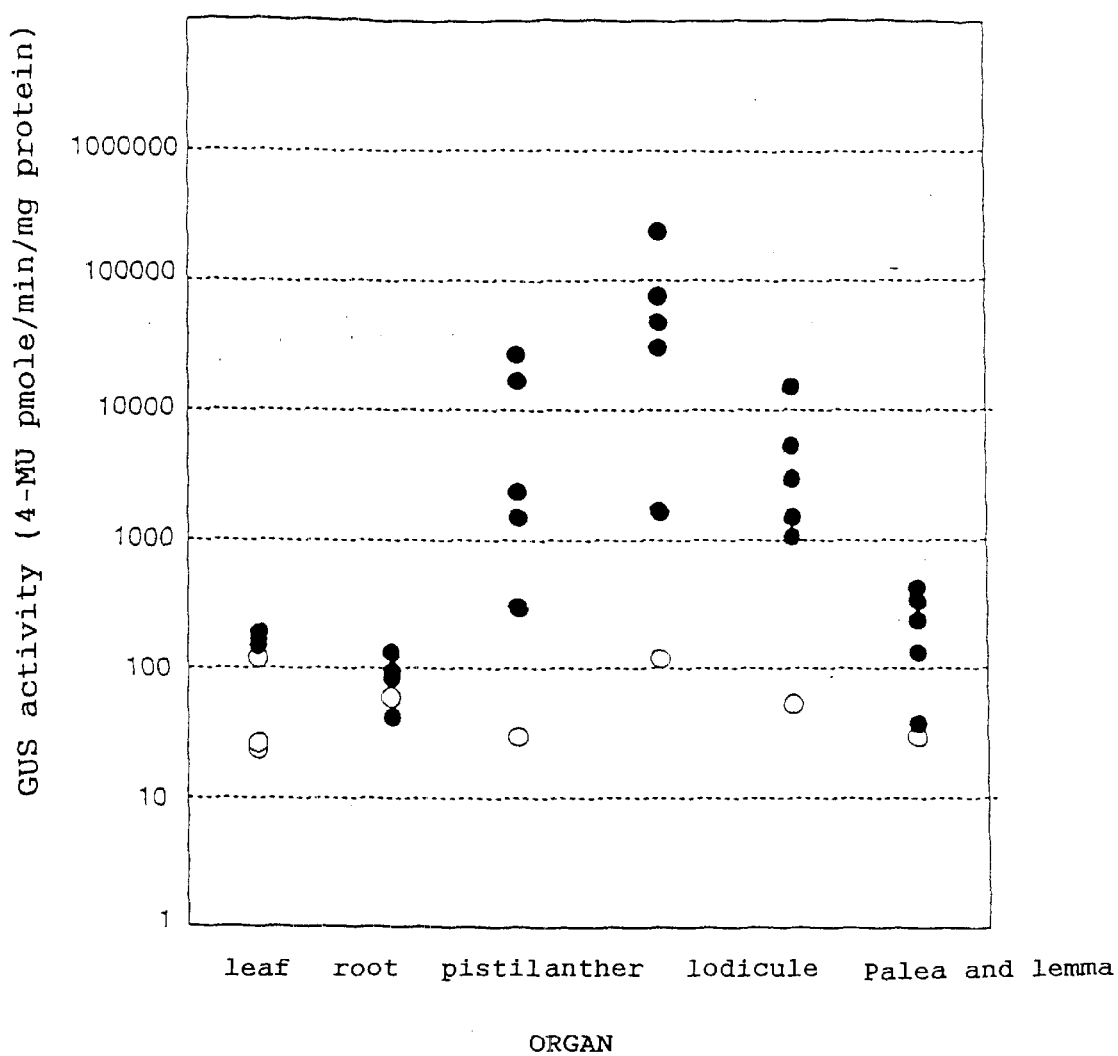
FIG. 10 is a graph showing the results of the measurement of the activity of RPC175 promoter in various rice organs.

From each of pYOT175IG-1 and pYOT175G-2, one line was selected so that the promoter expression sites as determined by the histological observation of GUS in the transformation generation would coincide well with the results of Northern analysis and RT-PCR. Then, the GUS expression in the next generation (R1 generation) was examined by the fluorescent analysis method with the use of MUG (4-methylumbelliferyl β-D-glucuronide) as the substrate. Leaf, root, pistil, anther (+filament), lodicule and palea and lemma were collected from one plant of the non-transformant, one R1 plant of the pYOT175IG-1 line and four R1 plants of the pYOT175G-2 line. Then protein was extracted from each plant and GUS was assayed. The results are shown in FIG. 10. The GUS activities in the leaf and root of the transformants were comparable to those of the non-transformant (18 to 210 units), while the GUS activities in pistil, anther and lodicule of the transformants were about 10 to 1,000 times as high as those of the non-transformant, though the activities varied from plant to plant. Namely, extremely high activities of 486 to 38,829 units, 1,044 to 14,496 units and 1,808 to 203,190 units per mg protein were observed respectively in pistil, lodicule and anther. [1 unit herein referrs to the activity by which 1 pmole of 4-MU (4-methylumbelliferone) is produce from MUG in 1 minute.] Also, in palea and lemma, activities (64 to 650 units) 1 to 10 times as high as that of the non-transformant were observed. These facts indicated that the flower organ-specific expression of the 175 promoter was stably maintained in the decendants of transfarmants.

Thus, it was confirmed by analyzing GUS in the generation of the transformation and the next generation that this promoter is one expressed specifically in flower organs.

Example 4

Assay for Chitinase Activity of 175 Protein (1) Expression of the Protein Encoded by RPC175 in *E. coli*

To examine whether the chitinase-like protein encoded by RPC175 would actually have chitinase activity or not, the 175 protein was first expressed in *E. coli* by using The QIA expressionist System (manufactured by QIAGEN).

i) Construction of Expression Vector

As an expression vector pQE30 was employed. In this vector, 6 histidine residues are positioned upstream of the multicloning site. Thus, a protein will be expressed, by using this vector, as a fused protein having a histidine tag at the N-terminus.

Figure 11:
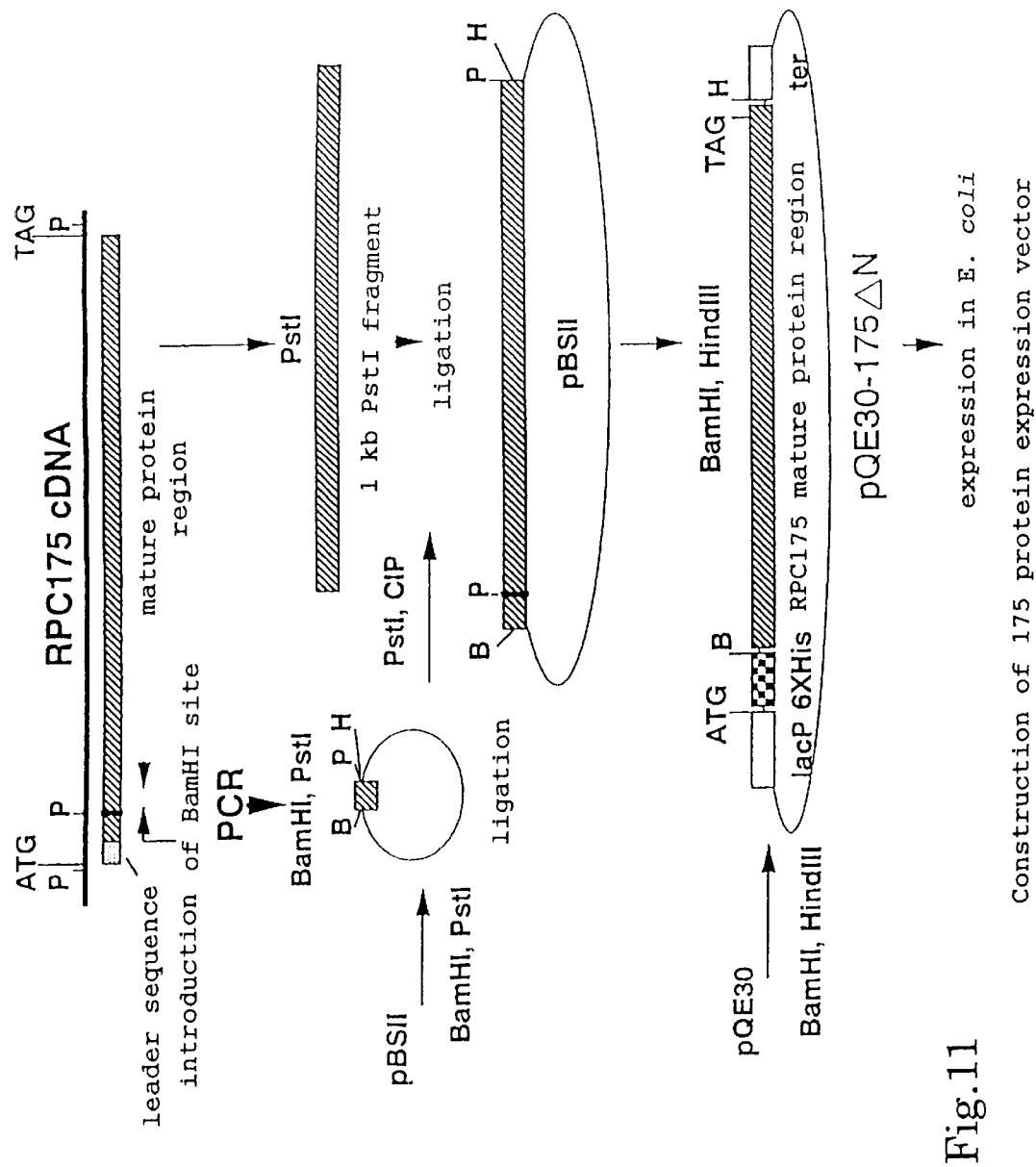
FIG. 11 is an illustration showing the procedure for constructing the vector for expressing the protein encoded by RPC175 gene.

FIG. 11 shows the procedure for the construction. RPC175 encodes a chitinase-like protein. By comparison with structures of other chitinases it was considered that RPC175 has a leader sequence consisting of 20 amino acids at the N-terminus. In the gene construction, this leader sequence was eliminated. First, RPC175 was digested with PstI to prepare a fragment of about 1 kb which contained almost all of the regions but a part of the N-terminal region of the mature protein. Separately, the following two primers were synthesized:

175mat5Bm (SEQ ID NO:18), 5'-GCGGGATCCGAGCAGTGCGGCAGGCAG-3';
C5FW2 (SEQ ID NO:19) 5'-TTGCAGTAGTCGTCGGTGAG-3';

and PCR was carried out to amplify the remaining part of N-terminus. The amplified product was digested with BamHI and PstI and subcloned into pBSII. After confirming the nucleotide sequence, this plasmid was digested with PstI and treated with CIP. Into this plasmid the above-mentioned PstI fragment of 1 kb was inserted to construct a plasmid containing the entire region of RPC175 mature protein. Next, this plasmid was digested with BamHI and HindIII and cloned into the vector pQE30 having been digested with the same enzymes. After confirming the nucleotide sequence, the vector thus obtained (named pQE30-175ΔN) was used in the expression in *E. coli*.

ii) Expression in *E. coli* and Purification of Protein

Figure 12:
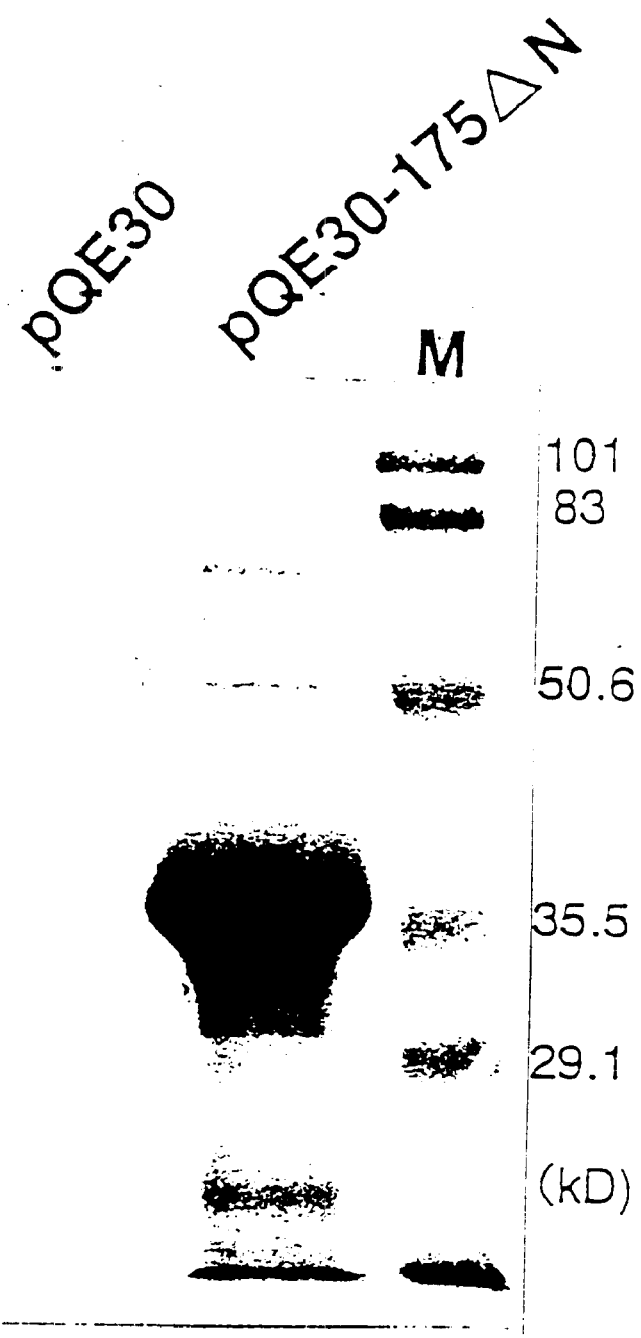
FIG. 12 consists of a photograph of SDS-PAGE pattern showing the results of the experiment on the expression of the protein encoded by RPC175 gene.

Competent cells of *E. coli* M15 were prepared and transformed by the expression vector constructed above. Plasmids were extracted from colonies of transformants and the introduction of the expression vector was confirmed. Subsequently, the *E. coli* cells were cultured and induced with IPTG in accordance with the protocol attached to the kit. Briefly, a 1/50 aliquot of the *E. coli* cells suspension cultured overnight was added to 50 ml of a 2XYT liquid medium containing ampicillin and kanamycin. After culturing for 2.5 hours, it was confirmed that the absorbance at 600 nm ($A_{600}$) reached about 0.5. Then 2 to 4 mM of IPTG was added and the culture was continued for additional 4.5 hours. In addition, two kinds of control cultures were included, namely, one which was free from IPTG-induction and the other which relates to *E. coli* transformed with the vector (pQE30) alone. The cells of each culture were collected by centrifugation and stored at −80° C. The extraction of crude proteins and the purification thereof with Ni-NTA Agarose (manufactured by QIAGEN) were each carried out in accordance with the manufacturer's protocol. The crude protein extract and the purified protein were electrophoresed on 12.5 to 15% SDS polyacrylamide gel according to the method of Laemmli (Nature 227, 680–685, 1970) and then stained with Coomassie brilliant blue (CBB) R250. As a result, no band seemingly assignable to the protein encoded by RPC175 was observed in the soluble protein fraction from any of the cultures. In contrast thereto, a band with somewhat larger in size than expected (i.e., 33 kD) was observed exclusively in the insoluble fraction of the induction-treated culture containing pQE30-175ΔN. Thus, the protein encoded by RPC175 was mostly insoluble. To solubilize this protein, it was necessary to add 8 M of urea to the buffer. However, the insoluble protein was expressed in a considerably large amount and could be purified on Ni-NTA Agarose. FIG. 12 shows the result of electrophoresis of ½ of the whole 175 protein purified from the cells cultured on a scale of 50 ml. Subsequently, to provide samples to be used for raising an antibody, the *E. coli* was cultured on a 250 ml-scale and the insoluble 175 protein was extracted and purified under the same conditions as those described above. Then the band of the expressed protein was cut from the polyacrylamide gel. The polyacrylamide gel band thus cut out was further minced into pieces with a razor, then transferred into an Eppendof tube to be ground in a homogenizer. After adding 10 times volume of a buffer (20 mM Tris pH 8.0, 1% SDS), the mixture was shaken at room temperature over one or two nights so as to elute the protein from the acrylamide gel. After removing the gel by centrifugation, the supernatant was dialyzed against 80% acetone overnight in a dialysis tube Spectra/Por1 MWCO:6-8,000 (manufactured by Spectrum Medical Industries). Next, the protein solution was recovered from the dialysis tube and dried.

The protein sample was suspended in 1×SDS Sample Buffer (Maniatis et al. 1982) and treated at 95° C. for 5 minutes. Next, the protein was electrophoresed on a 15% polyacrylamide gel. In order to confirm that the protein recovered from the cut out gel was in fact the desired one, Western blotting was performed with the use of Ni-NTA HRP conjudgate (manufactured by QIAGEN) as the antibody. On the other hand, the gel after the completion of the electrophoresis was stained with CBB and the protein concentration was estimated by comparing with markers of known concentrations (Prestained SDS-PAGE standards Low Range, manufactured by BIORAD).

iii) Production of Antibody

The production of antibody was undertaken by Sawady Technology Co., Ltd. When determined by ELISA, the rabbit antibody had a titer of 23,600. As a result of Western analysis with the use of HRP as the secondary antibody, this antibody reacted with the sample protein with a high sensitivity.

iv) Solubilization of Protein Encoded by RPC175

Figure 13:
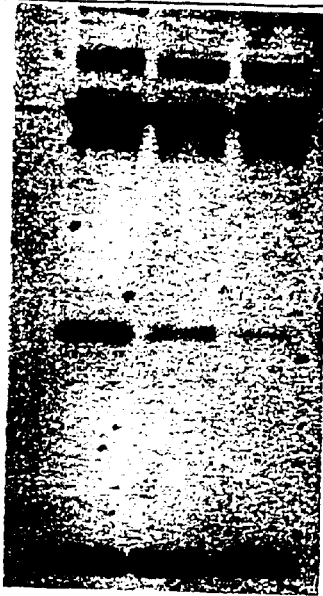
FIG. 13 consists of a photograph of Western analysis pattern showing the results of an experiment on the solubilization of the protein encoded by RPC175.

As described above, the protein encoded by RPC175, when expressed in *E. coli*, was mostly (99% or above) insoluble. When the soluble fraction was subjected to Western blotting with the use of the above-mentioned antibody, on the other hand, the 175 protein was detected though in a small amount. Moreover, it was also found that this protein contained in a trace amount could be purified on Ni-NTA Agarose. Generally speaking, when a foreign protein is expressed in *E. coli*, the protein often cannot assume the correct folded structure but forms inclusion bodies due to rapid induction of expression. This phenomenon can be avoided by employing milder induction conditions. To obtain a large amount of 175 protein in the soluble form, therefore, the following experiment was carried out with respect to the IPTC concentration and culture temperature which were the main factors of the induction conditions. Namely, the induction was performed under three conditions (at 37° C. with 2 mM of IPTG; at 25° C. with 0.5 mM of IPTG; and at 15° C. with 0.1 mM of IPTG). The culture was continued for 4.5 hours at 37° C. and 25° C. and for 18 hours at 15° C. After culturing under the conditions as specified above, the cells showed turbidities ($A_{600}$) of 1.04, 0.89 and 0.85 respectively at 37° C., 25° C. and 15° C. The *E. coli* cells (in 50 ml liquid culture medium:) which expressed the protein under these conditions were collected by centrifugation and stored at −80° C. From these cells, proteins were extracted by using a urea-free buffer solution in accordance with QIAGEN's instructions and the 175 protein carrying the HIS tag was purified with the use of Ni-NTA Agarose. Finally, the 175 protein was eluted from the Ni-NTA Agarose with 300 μl of a 0.1 M phosphate buffer (pH 4.5)

containing 10 mM of Tris. The eluate (10 μl) was electrophoresed on SDS-PAGE followed by Western analysis with the use of the above-mentioned antibody against the 175 protein. Since it was anticipated that the 175 protein in the samples was only in a trace amount, ECL+plus System (manufactured by Amersham) was used in the Western blotting. The primary and secondary antibodies were added each at a concentration of 1/10,000 and reacted each time for 1 hour with the ECL nitrocellulose membrane having the fractionated proteins blotted thereon. The reaction with the substrate was continued for 5 minutes and the X-ray film was exposed to light for 2 to 20 minutes. As a result, the densities of the bands assignable to the purified soluble 175 protein increased as the IPTG concentration and the culture temperature of E. Coli were lowered as shown in FIG. 13. The densities of these bands were compared with that of the bands of the above-mentioned 175 protein of a known concentration (prepared by dissolving 10 ng of the insoluble fraction prepared for the production of the antibody in 8 M urea) electrophoresed on the same gel. As a result, the soluble 175 protein was obtained in amounts of 97.6 ng, 12.4 ng and 2.1 ng in the order of how mild the culture conditions were. At the same time, 10 μl aliquots of the whole proteins eluted from the Ni-NTA Agarose gel were quantitated with Bio-Rad Protein Assay (manufactured by BIORAD). As a result, the protein contents were respectively 38 μg, 24 μg and 34 μg. Thus, the ratios of the 175 protein in the whole proteins eluted were calculated respectively as 2.57%, 0.52% and 0.06%. These results suggest that the ratio of the soluble 175 protein could be elevated by lowering the IPTG concentration and the culture temperature.

(2) Assay of Chitinase Activity of E. coli

Chitinase activity was assayed by the Reissig method by determining the saccharides solubilized from colloidal chitin as the substrate. The colloidal chitin was prepared in the following manner. Chitin powder 2 g was dissolved gradually in 100 ml of cold conc. hydrochloric acid while elevating temperature and then filtered through a G-3 glass filter. The filtrate was added slowly to 10 times volume of sterilized water and allowed to stand at 4° C. overnight to re-precipitate the chitin. After removing the supernatant, the precipitate was re-suspended in sterilized water and centrifuged at 6,000 g for 10 minutes. The washing was repeated until the pH of the supernatant became neutral. The precipitate was finally suspended in 150 ml of sterilized water to give a colloidal chitin solution.

The chitinase activity was measured in the following manner. A 100 μl aliquot of the enzyme solution and 100 μl of the colloidal chitin solution were mixed and incubated at 37° C. for 2 hours. After centrifuging at 6,000 rpm for 5 minutes, 150 μl of the supernatant was collected. As the blanc test same enzyme solution alone was incubated at 37° C. for 2 hours and then colloidal chitin was added immediately before centrifugation. To each of these supernatants, 15 μl of a 1 M phosphate buffer (pH 7.2) was added to adjust the pH value. Subsequently, 10 μl of 3% Helicase (manufactured by SIGMA) was added and the mixture was incubated at 37° C. for 1 hour to allow the chitin oligomers to be hydrolyzed. Next, 30 μl of 0.8 M potassium borate-KOH (pH 10.2) was added and the mixture was boiled for 3 minutes. Simultaneously, 25, 50 and 100 nmol N-acetylglucosamine (GlcNAC, manufactured by SIGMA) solubilized in the above assay reagents were also boiled to provide a standard curve. After the completion of boiling, the mixtures were immediately ice-cooled followed by addition of 1 ml of a solution of p-dimethyl aminobenzaldehyde (DMAB, manufactured by Wako Pure Chemical Industries, Inc.) prepared by dissolving 1 g of DMAB in 100 ml of acetic acid containing 1% of hydrochloric acid. After incubating at 37° C. for 20 minutes, the absorbance ($A_{585}$) was measured and the amount of GlcNAc was calculated from the standard curve. One unit is defined as the activity of the enzyme which cause solubilization of saccharides corresponding to 1 μmol of N-acetylglucosamine in 1 minute.

By this assay system, there were measured the chitinase activities of the purified 175 protein carrying the HIS tag produced by E. coli cells cultured under the above-mentioned three expression-inducing conditions. Further, the proteins in the two kinds of control cultures [i.e., one having E. Coli with the vector (pQE30) alone and the other being free from IPTG-induction] were extracted, purified and subjected to the assay. As a result, an apparent chitinase activity was detected in the test wherein pQE30-175ΔN was subjected to the induction of expression at the culture temperature of 15° C. and IPTG concentration of 0.1 mM. The enzyme activity in this culture was 1.9 mU/mg protein, i.e., 3 to 4 times as high as those in the control cultures (0 to 5.1 mU/mg protein). However, it is to be understood that this activity was based on the whole proteins eluted from the Ni-NTA Agarose. As described above, the 175 protein amounted to about 2.57% of the eluted proteins. Thus, it is estimated that the enzyme activity of the 175 protein is at least several ten mU/mg protein. In the test lot of the culture temperature of 25° C., a slight chitinase activity, compared with the control lots, was detected. However, the test lot of the culture temperature of 37° C. showed no activity. This is seemingly because the 175 protein subjected to the assay had only a low concentration.

Based on these results, it has been clarified that the chitinase-like protein encoded by RPC175 has actually a chitinase activity.

TABLE 2

Chitinase activity of protein encoded by RPC175 gene

| Culture temp. (° C.) | Expression vector | IPTC concn. (mM) | Activity (mU/mg protein) |
| --- | --- | --- | --- |
| 15 | pQE30 | 0 | 0 |
| 15 | pQE30 | 0.1 | 0.50 |
| 15 | pQE30-175ΔN | 0 | 0.51 |
| 15 | pQE30-175ΔN | 0.1 | 1.90 |
| 25 | pQE30 | 0 | 0.99 |
| 25 | pQE30 | 0.5 | 1.04 |
| 25 | pQE30-175ΔN | 0 | 1.48 |
| 25 | pQE30-175ΔN | 0.5 | 1.62 |
| 37 | pQE30 | 0 | 0.35 |
| 37 | pQE30 | 2 | 0.72 |
| 37 | pQE30-175ΔN | 0 | 0.62 |
| 37 | pQE30-175ΔN | 2 | 0.68 |

EFFECTS OF THE INVENTION

According to the present invention, it becomes possible to genetically manipulate flower organs not only anther but also pistil or lodicule of plants. Thus female sterile plants and rice plants with exposed stigma may be constructed. Also, the flowering characteristics may be physiologically regulated. The present invention further makes it possible to construct plants which are resistant against pathogenic bacteria and fungi containing chitin.

What is claimed is:

1. An isolated DNA fragment comprising the sequence from position 1 to 1234 in the nucleotide sequence of SEQ ID NO: 3, or a part of said sequence having a promoter activity specific to a floral organ.

2. An isolated DNA fragment as claimed in claim 1, wherein said part of the sequence from positions 1 to 1234 in the nucleotide sequence of SEQ ID NO:3 is a sequence from the upstream region of the transcription initiation point.

3. An isolated DNA fragment as claimed in claim 1, wherein said part comprises a sequence of 500 contiguous nucleotides which precedes the transcription initiation point.

4. An isolated DNA fragment comprising the sequence from position 1 to 1140 in the nucleotide sequence of SEQ ID NO: 3, or a part of said sequence having a promoter activity specific to a floral organ.

5. An isolated DNA fragment comprising the sequence from position 1 to 1121 in the nucleotide sequence of SEQ ID NO: 3, or a part of said sequence having a promoter activity specific to a floral organ.

6. An isolated DNA fragment comprising a nucleotide sequence which is hybridizable under the following conditions of hybridization and washing:

hybridization: 0.25 M $Na_2HPO_4$, pH 7.2, 7% SDS, 1 mM EDTA, 1×Denhardt's solution, 68° C., overnight;

washing: 20 mM $Na_2HPO_4$, pH 7.2, 1% SDS, 1 mM EDTA, 68° C., 15 min. twice.

with a DNA sequence comprising the sequence from positions 1 to 1234 in the nucleotide sequence of SEQ ID NO: 3, wherein said hybidizable sequence has a promoter activity specific to a floral organ.

7. The isolated DNA fragment of claim 6, wherein said DNA fragment is ligated to a gene, and said gene is a structural gene that codes for a protein capable of inducing the sterility in plants.

8. The isolated DNA fragment of claim 6, wherein said DNA fragment is ligated to a gene, and said gene codes for a protein that is capable of promoting the elongation or division of plant cells.

9. The isolated DNA fragment of claim 6, wherein said DNA fragment is ligated to a gene, and said gene codes for a protein that improves tolerance to herbicides or diseases.

10. An isolated DNA fragment comprising a nucleotide sequence which is hybridizable under the following conditions of hybridization and washing:

hybridization: 5×SSC, 5×Denhardt's solution, 1% SDS, 68° C., overnight;

washing: 0.2×SSC, 0.1% SDS, 42° C., 15 min. twice;

with a DNA sequence comprising the sequence from positions 1 to 1234 in the nucleotide sequence of SEQ ID NO: 3, wherein said hybridizable sequence has a flower organ-specific promoter activity.

11. The isolated DNA fragment as claimed in claim 6 which comprises positions 300–1234 nucleotides of SEQ ID NO:3.

* * * * *

SEQUENCE LISTING

<160> NUMBER OF SEQ ID NOS: 19

<210> SEQ ID NO 1
<211> LENGTH: 1318
<212> TYPE: DNA
<213> ORGANISM: Oryza sativa
<220> FEATURE:
<221> NAME/KEY: CDS
<222> LOCATION: (114)..(1097)
<220> FEATURE:
<223> OTHER INFORMATION: Clone: RPC175; Library: ZAPII cDNA library from pistil mRNA; Strain: IR24;

<400> SEQUENCE: 1

```
atcactcacc agctacgtac actcaaccaa cacaccactg aaaagcaaga ttttgttgaa      60
gaaataagca tcttgccatg atcgcagcaa gggctgcaaa cctgcaggtg gcc atg        116
                                                             Met
                                                             1 aag gcc ctg gcg ctg gcc gtg ctg gcc ctc gcc tac gcc gcg gcg acg       164
Lys Ala Leu Ala Leu Ala Val Leu Ala Leu Ala Tyr Ala Ala Ala Thr
          5                  10                  15 gcg cgc gcc gag cag tgc ggc agg cag gcc ggc ggc gcc agg tgc ccc       212
Ala Arg Ala Glu Gln Cys Gly Arg Gln Ala Gly Gly Ala Arg Cys Pro
     20                  25                  30 aac agg ctc tgc tgc agc agg tgg ggg tgg tgc ggc ctc acc gac gac       260
Asn Arg Leu Cys Cys Ser Arg Trp Gly Trp Cys Gly Leu Thr Asp Asp
 35                  40                  45 tac tgc aag ggc ggc tgc cag agc cag tgc cgc gtc tcc cgc gac ggc       308
Tyr Cys Lys Gly Gly Cys Gln Ser Gln Cys Arg Val Ser Arg Asp Gly
 50                  55                  60                  65 ggc gac gac gac gtc gcc gcg gtg ctg ctc acg gcg ccg ggc ggc ggc       356
Gly Asp Asp Asp Val Ala Ala Val Leu Leu Thr Ala Pro Gly Gly Gly
                 70                  75                  80 cgc gcc ggc gtg gcg tcc gtc gtg acg tcg gac cag ttc gag cgc atg       404
Arg Ala Gly Val Ala Ser Val Val Thr Ser Asp Gln Phe Glu Arg Met
             85                  90                  95 ctg ccc cac cgc gac gac gcg gcg tgc ccc gcc cgc ggg ttc tac gcc       452
Leu Pro His Arg Asp Asp Ala Ala Cys Pro Ala Arg Gly Phe Tyr Ala
            100                 105                 110 tac cgc gcc ttc gtc gcc gcc gcc ggc gcg ttc ccg gcc ttc gcc gcc       500
Tyr Arg Ala Phe Val Ala Ala Ala Gly Ala Phe Pro Ala Phe Ala Ala
        115                 120                 125 acg ggc gac gcc gac acc cgc aag cgt gag gtc gcc gcg ttc ctg gcc       548
Thr Gly Asp Ala Asp Thr Arg Lys Arg Glu Val Ala Ala Phe Leu Ala
130                 135                 140                 145 cag act tcc cac gcg acc tct ggt ggg ccc tac tcg tgg ggc tac tgc       596
Gln Thr Ser His Ala Thr Ser Gly Gly Pro Tyr Ser Trp Gly Tyr Cys
                150                 155                 160 tac aag gag gtg aag ggc gcg acg tca gac ttc tgc gtg ccg aac gcg       644
Tyr Lys Glu Val Lys Gly Ala Thr Ser Asp Phe Cys Val Pro Asn Ala
            165                 170                 175 cgc tgg ccg tgc gcg ccc ggc aag gcg tac cac gcc cgc gga ccc atg       692
Arg Trp Pro Cys Ala Pro Gly Lys Ala Tyr His Ala Arg Gly Pro Met
        180                 185                 190 caa atc gca tac aac tac aac tat ggg gcg gcc ggc gag gcg atc ggc       740
Gln Ile Ala Tyr Asn Tyr Asn Tyr Gly Ala Ala Gly Glu Ala Ile Gly
    195                 200                 205 gcg gac ctg ctg ggc aac ccg gag ctg gtg gca acg gac ccg acg gtg       788
Ala Asp Leu Leu Gly Asn Pro Glu Leu Val Ala Thr Asp Pro Thr Val
210                 215                 220                 225
```

```
gcg ttc aag acg gcg ctg tgg ctg tgg atg acc gcg cgg tcg ccg agc            836
Ala Phe Lys Thr Ala Leu Trp Leu Trp Met Thr Ala Arg Ser Pro Ser
            230                 235                 240 cag ccg tcg ccg cac gcc gtc gtc acg ggg cag tgg act ccg act ccc            884
Gln Pro Ser Pro His Ala Val Val Thr Gly Gln Trp Thr Pro Thr Pro
            245                 250                 255 gcg gac agc gcg gcc ggc cgc gcg cca ggc tac ggg ctc acc acg aac            932
Ala Asp Ser Ala Ala Gly Arg Ala Pro Gly Tyr Gly Leu Thr Thr Asn
            260                 265                 270 atc ctc acc ggc ggg ctc cag tgc gcc ggc ggc aac ggc ggc gcc gac            980
Ile Leu Thr Gly Gly Leu Gln Cys Ala Gly Gly Asn Gly Gly Ala Asp
            275                 280                 285 cgg gtc gcg ttc tac aag cgc tac tgc gac gtg ctc ggc gtc ggc tac           1028
Arg Val Ala Phe Tyr Lys Arg Tyr Cys Asp Val Leu Gly Val Gly Tyr
290                 295                 300                 305 ggg ccc aac ctg gac tgc ttc ggc cag gcg ccg ttc gac ggc gac atc           1076
Gly Pro Asn Leu Asp Cys Phe Gly Gln Ala Pro Phe Asp Gly Asp Ile
            310                 315                 320 atg tcg gcg tct gcg gcg aag tagacgtgtg cgccgccgtg ccggccccga              1127
Met Ser Ala Ser Ala Ala Lys
            325 tcgatcgaat aaaattgcgt gtgagtacgc acttcgcacg gtcgctctgc agccagagtg         1187 agtgagtttg ctttatgtat ttttcggttt cgggcgagga attcttcatg gatctgtgaa         1247 agcccatatg tatgcatggt catggcatga ataaagtagt actgatcttc tcgaaaaaaa         1307 aaaaaaaaaa a                                                              1318

<210> SEQ ID NO 2
<211> LENGTH: 328
<212> TYPE: PRT
<213> ORGANISM: Oryza sativa
<220> FEATURE:
<223> OTHER INFORMATION: Clone: RPC175; Library: ZAPII cDNA library from
      pistil mRNA; Strain: IR24;

<400> SEQUENCE: 2

Met Lys Ala Leu Ala Leu Ala Val Leu Ala Leu Ala Tyr Ala Ala Ala
 1               5                  10                  15

Thr Ala Arg Ala Glu Gln Cys Gly Arg Gln Ala Gly Gly Ala Arg Cys
            20                  25                  30

Pro Asn Arg Leu Cys Cys Ser Arg Trp Gly Trp Cys Gly Leu Thr Asp
        35                  40                  45

Asp Tyr Cys Lys Gly Gly Cys Gln Ser Gln Cys Arg Val Ser Arg Asp
    50                  55                  60

Gly Gly Asp Asp Asp Val Ala Ala Val Leu Leu Thr Ala Pro Gly Gly
65                  70                  75                  80

Gly Arg Ala Gly Val Ala Ser Val Val Thr Ser Asp Gln Phe Glu Arg
                85                  90                  95

Met Leu Pro His Arg Asp Asp Ala Ala Cys Pro Ala Arg Gly Phe Tyr
            100                 105                 110

Ala Tyr Arg Ala Phe Val Ala Ala Gly Ala Phe Pro Ala Phe Ala
        115                 120                 125

Ala Thr Gly Asp Ala Asp Thr Arg Lys Arg Glu Val Ala Ala Phe Leu
    130                 135                 140

Ala Gln Thr Ser His Ala Thr Ser Gly Gly Pro Tyr Ser Trp Gly Tyr
145                 150                 155                 160

Cys Tyr Lys Glu Val Lys Gly Ala Thr Ser Asp Phe Cys Val Pro Asn
```

|  |  | 165 |  |  | 170 |  |  | 175 |  |  |  |
|---|---|---|---|---|---|---|---|---|---|---|---|

Ala Arg Trp Pro Cys Ala Pro Gly Lys Ala Tyr His Ala Arg Gly Pro
            180                    185                190

Met Gln Ile Ala Tyr Asn Tyr Asn Tyr Gly Ala Ala Gly Glu Ala Ile
       195                 200               205

Gly Ala Asp Leu Leu Gly Asn Pro Glu Leu Val Ala Thr Asp Pro Thr
   210                  215               220

Val Ala Phe Lys Thr Ala Leu Trp Leu Trp Met Thr Ala Arg Ser Pro
225             230               235            240

Ser Gln Pro Ser Pro His Ala Val Val Thr Gly Gln Trp Thr Pro Thr
            245               250            255

Pro Ala Asp Ser Ala Ala Gly Arg Ala Pro Gly Tyr Gly Leu Thr Thr
         260              265               270

Asn Ile Leu Thr Gly Gly Leu Gln Cys Ala Gly Gly Asn Gly Gly Ala
       275              280               285

Asp Arg Val Ala Phe Tyr Lys Arg Tyr Cys Asp Val Leu Gly Val Gly
   290                  295               300

Tyr Gly Pro Asn Leu Asp Cys Phe Gly Gln Ala Pro Phe Asp Gly Asp
305             310               315            320

Ile Met Ser Ala Ser Ala Ala Lys
            325

<210> SEQ ID NO 3
<211> LENGTH: 2636
<212> TYPE: DNA
<213> ORGANISM: Oryza sativa
<220> FEATURE:
<221> NAME/KEY: CDS
<222> LOCATION: (1235)..(1691)
<220> FEATURE:
<221> NAME/KEY: CDS
<222> LOCATION: (1777)..(1909)
<220> FEATURE:
<221> NAME/KEY: CDS
<222> LOCATION: (2109)..(2502)
<220> FEATURE:
<223> OTHER INFORMATION: Clone: RPG102; Library: dashII genomic library
     from green leaf genome DNA; Strain: IR24

<400> SEQUENCE: 3

| | | | | |
|---|---|---|---|---|
| gaattcatat | ctatcataca | aagagatcta | ggttgcattt | cttcatatag | atcctgtctc | 60 |
| atcctgggta | gttgtaacgc | aaactttcca | acgaatcaaa | ccagagcacg | gctcgatctg | 120 |
| gctgatgcat | gtgtgacatc | gaatcccagg | aaacaaagac | gatcgttttc | actactgttc | 180 |
| tatctcttca | tctagtttaa | ttaatgccct | gtatattcga | tcgtgcatcc | atgtatcagt | 240 |
| gggctcagtt | aaacaaagca | gacgcaggca | tgcaggagat | gaaaacgagc | aacgcaccct | 300 |
| cgtgctgccc | gaaagacagt | gtactctcca | cactggcatg | actcatttct | acgggtgaaa | 360 |
| acagagcgga | ttcagacaga | taatggtcat | accatatcct | aaaccatatt | ttttaagcgg | 420 |
| attcagagtg | ggtgcggata | ggatacggat | gcgcatgcgg | agaggattat | ttcggatgtc | 480 |
| ggaaatggtg | cggaatcagt | tcgaaaaaga | ttaaatttat | cggatgttac | atgtgtatac | 540 |
| aatcaataca | atattaagtt | agcaatgcaa | gaaacaataa | tacaataatc | aataaacgat | 600 |
| ccatcatact | aattatgtgc | ttaagtgtta | aacaatatga | atacatgatg | tctataatat | 660 |
| aaaaatacag | ctacgcaagt | atgccatgag | aaggtgaaag | cctcagacta | agaaatctat | 720 |
| gctaattgat | aaattagtac | attggataga | ccaacttatg | ttatatgcaa | tagatagagt | 780 |

-continued

```
gattacatgt gttgataaat tcgaattatc cggcaaacgg ccaatcggat aatccgatag    840
aaatgtcgga taatctgcat ccaccggatt ttagagatac catatcctca tccgcatccg    900
cattatacta tcctcatccg cattcatatc cgccggattt ctaaaagccc ataccatatc    960
ctcgtttgga acggattcgg agtggatcgg atctatccga tcggttttca ctcctactca   1020
tttcacacaa gatgaggcca tcaccttgca taaccgattt tacacaagct agatgaggcc   1080
atgatctcct ctatataaga ggccatgcag tctgtggctt catcactcac cagctacgta   1140
cactcaacca acacaccact gaaaagcaag attttgttga agaaataagc atcttgccat   1200
gatcgcagca agggctgcaa acctgcaggt ggcc atg aag gcc ctg gcg ctg gcc   1255
                                    Met Lys Ala Leu Ala Leu Ala
                                      1               5 gtg ctg gcc ctc gcc tac gcc gcg gcg acg gcg cgc gcc gag cag tgc     1303
Val Leu Ala Leu Ala Tyr Ala Ala Ala Thr Ala Arg Ala Glu Gln Cys
             10                  15                  20 ggc agg cag gcc ggc ggc gcc agg tgc ccc aac agg ctc tgc tgc agc     1351
Gly Arg Gln Ala Gly Gly Ala Arg Cys Pro Asn Arg Leu Cys Cys Ser
     25                  30                  35 agg tgg ggg tgg tgc ggc ctc acc gac gac tac tgc aag ggc ggc tgc     1399
Arg Trp Gly Trp Cys Gly Leu Thr Asp Asp Tyr Cys Lys Gly Gly Cys
 40                  45                  50                  55 cag agc cag tgc cgc gtc tcc cgc gac ggc ggc gac gac gac gtc gcc     1447
Gln Ser Gln Cys Arg Val Ser Arg Asp Gly Gly Asp Asp Asp Val Ala
             60                  65                  70 gcg gtg ctg ctc acg gcg ccg ggc ggc ggc cgc gcc ggc gtg gcg tcc     1495
Ala Val Leu Leu Thr Ala Pro Gly Gly Gly Arg Ala Gly Val Ala Ser
         75                  80                  85 gtc gtg acg tcg gac cag ttc gag cgc atg ctg ccc cac cgc gac gac     1543
Val Val Thr Ser Asp Gln Phe Glu Arg Met Leu Pro His Arg Asp Asp
     90                  95                 100 gcg gcg tgc ccc gcc cgc ggg ttc tac gcc tac cgc gcc ttc gtc gcc     1591
Ala Ala Cys Pro Ala Arg Gly Phe Tyr Ala Tyr Arg Ala Phe Val Ala
105                 110                 115 gcg gcc ggc gcg ttc ccg gcc ttc gcc gcc acg ggc gac gcc gac acc     1639
Ala Ala Gly Ala Phe Pro Ala Phe Ala Ala Thr Gly Asp Ala Asp Thr
120                 125                 130                 135 cgc aag cgt gag gtc gcc gcg ttc ctg gcc cag act tcc cac gcg acc     1687
Arg Lys Arg Glu Val Ala Ala Phe Leu Ala Gln Thr Ser His Ala Thr
             140                 145                 150 tct g gtaacgtagt aacgtttact tgtcacgttg aactcacgt gtacgtacac          1741
Ser atgtcttatg cacgagtgcg catgtgtccc tgcag gt ggg ccc tac tcg tgg ggc   1796
                                         Gly Gly Pro Tyr Ser Trp Gly
                                                             155 tac tgc tac aag gag gtg aag ggc gcg acg tca gac ttc tgc gtg ccg     1844
Tyr Cys Tyr Lys Glu Val Lys Gly Ala Thr Ser Asp Phe Cys Val Pro
160                 165                 170                 175 aac gcg cgc tgg ccg tgc gcg ccc ggc aag gcg tac cac gcc cgc gga     1892
Asn Ala Arg Trp Pro Cys Ala Pro Gly Lys Ala Tyr His Ala Arg Gly
             180                 185                 190 ccc atg caa atc gca ta gtaagagaac gcaaggagc aaaccaaaac              1939
Pro Met Gln Ile Ala Tyr
                195 gtccatataa atgaacttgc aaacaaaaaa tccacaaaat ggacgaacac tagaaaaatc   1999 ttaaaatgca acgggatttc atccgtgaaa cgttcaattt cgagactagt actatttgga   2059 ctgaacaaat gacaaactac tggaatctaa ttttcaaatt caatttcag c aac tac     2115
                                                        Asn Tyr
```

-continued

```
aac tat ggg gcg gcc ggc gag gcg atc ggc gcg gac ctg ctg ggc aac     2163
Asn Tyr Gly Ala Ala Gly Glu Ala Ile Gly Ala Asp Leu Leu Gly Asn
200                 205                 210                 215 ccg gag ctg gtg gca acg gac ccg acg gtg gcg ttc aag acg gcg ctg     2211
Pro Glu Leu Val Ala Thr Asp Pro Thr Val Ala Phe Lys Thr Ala Leu
                220                 225                 230 tgg ctg tgg atg acc gcg cgg tcg ccg agc cag ccg tcg ccg cac gcc     2259
Trp Leu Trp Met Thr Ala Arg Ser Pro Ser Gln Pro Ser Pro His Ala
            235                 240                 245 gtc gtc acg ggg cag tgg act ccg act ccc gcg gac agc gcg gcc ggc     2307
Val Val Thr Gly Gln Trp Thr Pro Thr Pro Ala Asp Ser Ala Ala Gly
        250                 255                 260 cgc gcg cca ggc tac ggg ctc acc acg aac atc ctc acc ggc ggg ctc     2355
Arg Ala Pro Gly Tyr Gly Leu Thr Thr Asn Ile Leu Thr Gly Gly Leu
    265                 270                 275 cag tgc gcc ggc ggc aac ggc ggc gcc gac cgg gtc gcg ttc tac aag     2403
Gln Cys Ala Gly Gly Asn Gly Gly Ala Asp Arg Val Ala Phe Tyr Lys
280                 285                 290                 295 cgc tac tgc gac gtg ctc ggc gtc ggc tac ggg ccc aac ctg gac tgc     2451
Arg Tyr Cys Asp Val Leu Gly Val Gly Tyr Gly Pro Asn Leu Asp Cys
                300                 305                 310 ttc ggc cag gcg ccg ttc gac ggc gac atc atg tcg gcg tct gcg gcg     2499
Phe Gly Gln Ala Pro Phe Asp Gly Asp Ile Met Ser Ala Ser Ala Ala
            315                 320                 325 aag tagacgtgtg cgccgccgtg ccggccccga tcgatcgaat aaaattgcgt          2552
Lys gtgagtacgc acttcgcacg gtcgctctgc agccagagtg agtgagtttg ctttatgtat   2612
ttttcggttt cgggcgagga attc                                          2636

<210> SEQ ID NO 4
<211> LENGTH: 328
<212> TYPE: PRT
<213> ORGANISM: Oryza sativa
<220> FEATURE:
<223> OTHER INFORMATION: Clone: RPG102; Library: dashII genomic library
      from green leaf genome DNA; Strain: IR24

<400> SEQUENCE: 4

Met Lys Ala Leu Ala Leu Ala Val Leu Ala Leu Ala Tyr Ala Ala Ala
 1               5                  10                  15

Thr Ala Arg Ala Glu Gln Cys Gly Arg Gln Ala Gly Gly Ala Arg Cys
            20                  25                  30

Pro Asn Arg Leu Cys Cys Ser Arg Trp Gly Trp Cys Gly Leu Thr Asp
        35                  40                  45

Asp Tyr Cys Lys Gly Gly Cys Gln Ser Gln Cys Arg Val Ser Arg Asp
    50                  55                  60

Gly Gly Asp Asp Val Ala Ala Val Leu Leu Thr Ala Pro Gly Gly
65                  70                  75                  80

Gly Arg Ala Gly Val Ala Ser Val Val Thr Ser Asp Gln Phe Glu Arg
                85                  90                  95

Met Leu Pro His Arg Asp Asp Ala Ala Cys Pro Ala Arg Gly Phe Tyr
            100                 105                 110

Ala Tyr Arg Ala Phe Val Ala Ala Gly Ala Phe Pro Ala Phe Ala
    115                 120                 125

Ala Thr Gly Asp Ala Asp Thr Arg Lys Arg Glu Val Ala Ala Phe Leu
130                 135                 140

Ala Gln Thr Ser His Ala Thr Ser Gly Gly Pro Tyr Ser Trp Gly Tyr
```

```
                145                 150                 155                 160
Cys Tyr Lys Glu Val Lys Gly Ala Thr Ser Asp Phe Cys Val Pro Asn
                    165                 170                 175
Ala Arg Trp Pro Cys Ala Pro Gly Lys Ala Tyr His Ala Arg Gly Pro
                180                 185                 190
Met Gln Ile Ala Tyr Asn Tyr Asn Tyr Gly Ala Ala Gly Glu Ala Ile
            195                 200                 205
Gly Ala Asp Leu Leu Gly Asn Pro Glu Leu Val Ala Thr Asp Pro Thr
        210                 215                 220
Val Ala Phe Lys Thr Ala Leu Trp Leu Trp Met Thr Ala Arg Ser Pro
225                 230                 235                 240
Ser Gln Pro Ser Pro His Ala Val Val Thr Gly Gln Trp Thr Pro Thr
                245                 250                 255
Pro Ala Asp Ser Ala Ala Gly Arg Ala Pro Gly Tyr Gly Leu Thr Thr
            260                 265                 270
Asn Ile Leu Thr Gly Gly Leu Gln Cys Ala Gly Gly Asn Gly Gly Ala
        275                 280                 285
Asp Arg Val Ala Phe Tyr Lys Arg Tyr Cys Asp Val Leu Gly Val Gly
    290                 295                 300
Tyr Gly Pro Asn Leu Asp Cys Phe Gly Gln Ala Pro Phe Asp Gly Asp
305                 310                 315                 320
Ile Met Ser Ala Ser Ala Ala Lys
                325

<210> SEQ ID NO 5
<211> LENGTH: 25
<212> TYPE: DNA
<213> ORGANISM: Oryza sativa
<220> FEATURE:
<223> OTHER INFORMATION: RPC15
<220> FEATURE:
<223> OTHER INFORMATION: any n = g, c, a, t

<400> SEQUENCE: 5
gtcagacacn nagtagtgag tggtc                                          25

<210> SEQ ID NO 6
<211> LENGTH: 12
<212> TYPE: DNA
<213> ORGANISM: Oryza sativa
<220> FEATURE:
<223> OTHER INFORMATION: RPC17

<400> SEQUENCE: 6
tcatcactca cc                                                        12

<210> SEQ ID NO 7
<211> LENGTH: 29
<212> TYPE: DNA
<213> ORGANISM: Artificial Sequence
<220> FEATURE:
<220> FEATURE:
<223> OTHER INFORMATION: Description of Artificial Sequence:plasmid
      psB24

<400> SEQUENCE: 7
tacctagaac atggatccct acagcgtaa                                      29

<210> SEQ ID NO 8
<211> LENGTH: 35
<212> TYPE: DNA
```

<213> ORGANISM: Artificial Sequence
<220> FEATURE:
<220> FEATURE:
<223> OTHER INFORMATION: Description of Artificial Sequence:plasmid
      psB24

<400> SEQUENCE: 8
ctgcaccccg ggggatccac tagttctaga acatg                          35

<210> SEQ ID NO 9
<211> LENGTH: 61
<212> TYPE: DNA
<213> ORGANISM: Artificial Sequence
<220> FEATURE:
<220> FEATURE:
<223> OTHER INFORMATION: Description of Artificial Sequence:plasmid
      psB21

<400> SEQUENCE: 9
ctgcagcccg ggggatccac tagttctaga ggatcccccg ggtggtcagt cccttatgtt  60
a                                                                  61

<210> SEQ ID NO 10
<211> LENGTH: 17
<212> TYPE: DNA
<213> ORGANISM: Artificial Sequence
<220> FEATURE:
<220> FEATURE:
<223> OTHER INFORMATION: Description of Artificial Sequence:synthetic
      primer 75RV1

<400> SEQUENCE: 10
gacacccgca agcgtga                                              17

<210> SEQ ID NO 11
<211> LENGTH: 17
<212> TYPE: DNA
<213> ORGANISM: Artificial Sequence
<220> FEATURE:
<220> FEATURE:
<223> OTHER INFORMATION: Description of Artificial Sequence:synthetic
      primer 75FW1

<400> SEQUENCE: 11
cccttcacct ccttgta                                              17

<210> SEQ ID NO 12
<211> LENGTH: 24
<212> TYPE: DNA
<213> ORGANISM: Artificial Sequence
<220> FEATURE:
<220> FEATURE:
<223> OTHER INFORMATION: Description of Artificial Sequence:synthetic
      primer

<400> SEQUENCE: 12
gtatccatga gactacatac aact                                      24

<210> SEQ ID NO 13
<211> LENGTH: 22
<212> TYPE: DNA
<213> ORGANISM: Artificial Sequence
<220> FEATURE:
<220> FEATURE:
<223> OTHER INFORMATION: Description of Artificial Sequence:synthetic
      primer

<400> SEQUENCE: 13

```
tactcagcct tggcaatcca ca                                              22

<210> SEQ ID NO 14
<211> LENGTH: 21
<212> TYPE: DNA
<213> ORGANISM: Artificial Sequence
<220> FEATURE:
<220> FEATURE:
<223> OTHER INFORMATION: Description of Artificial Sequence:synthetic
      primer 175RV1

<400> SEQUENCE: 14
gacatcatgt cggcgtctgc g                                               21

<210> SEQ ID NO 15
<211> LENGTH: 23
<212> TYPE: DNA
<213> ORGANISM: Artificial Sequence
<220> FEATURE:
<220> FEATURE:
<223> OTHER INFORMATION: Description of Artificial Sequence:synthetic
      primer 175FW1

<400> SEQUENCE: 15
gccatgacca tgcatacata tgg                                             23

<210> SEQ ID NO 16
<211> LENGTH: 24
<212> TYPE: DNA
<213> ORGANISM: Artificial Sequence
<220> FEATURE:
<220> FEATURE:
<223> OTHER INFORMATION: Description of Artificial Sequence:synthetic
      primer C5FW

<400> SEQUENCE: 16
cttcatggcc acctgcaggt ttgc                                            24

<210> SEQ ID NO 17
<211> LENGTH: 19
<212> TYPE: DNA
<213> ORGANISM: Artificial Sequence
<220> FEATURE:
<220> FEATURE:
<223> OTHER INFORMATION: Description of Artificial Sequence:synthetic
      primer p3FW2

<400> SEQUENCE: 17
tgcgatcatg gcaagatgc                                                  19

<210> SEQ ID NO 18
<211> LENGTH: 27
<212> TYPE: DNA
<213> ORGANISM: Artificial Sequence
<220> FEATURE:
<220> FEATURE:
<223> OTHER INFORMATION: Description of Artificial Sequence:synthetic
      primer 175mat5Bm

<400> SEQUENCE: 18
gcgggatccg agcagtgcgg caggcag                                         27

<210> SEQ ID NO 19
<211> LENGTH: 20
<212> TYPE: DNA
<213> ORGANISM: Artificial Sequence
<220> FEATURE:
```

```
<220> FEATURE:
<223> OTHER INFORMATION: Description of Artificial Sequence:synthetic
      primer C5FW2

<400> SEQUENCE: 19
ttgcagtagt cgtcggtgag                                                    20
```